US011793566B2

(12) United States Patent
Hancock et al.

(10) Patent No.: US 11,793,566 B2
(45) Date of Patent: Oct. 24, 2023

(54) ELECTROSURGICAL INSTRUMENT

(71) Applicant: CREO MEDICAL LIMITED, Monmouth (GB)

(72) Inventors: Christopher Hancock, Bath (GB); Steven Morris, Chepstow (GB); Patrick Burn, Chepstow (GB); Louis Turner, Chepstow (GB); George Ullrich, Bangor (GB); David Webb, Bangor (GB)

(73) Assignee: CREO MEDICAL LIMITED, Chepstow (GB)

( * ) Notice: Subject to any disclaimer, the term of this patent is extended or adjusted under 35 U.S.C. 154(b) by 125 days.

(21) Appl. No.: 17/349,426

(22) Filed: Jun. 16, 2021

(65) Prior Publication Data
US 2021/0307821 A1    Oct. 7, 2021

Related U.S. Application Data

(62) Division of application No. 15/769,685, filed as application No. PCT/EP2016/074947 on Oct. 18, 2016, now Pat. No. 11,058,483.

(30) Foreign Application Priority Data

Oct. 19, 2015  (GB) .................................... 1518468

(51) Int. Cl.
*A61B 18/14* (2006.01)
*A61B 18/18* (2006.01)
(Continued)

(52) U.S. Cl.
CPC ...... *A61B 18/1492* (2013.01); *A61B 18/1206* (2013.01); *A61B 18/1815* (2013.01);
(Continued)

(58) Field of Classification Search
CPC ............ A61B 18/1206; A61B 18/1492; A61B 18/1815; A61B 2017/0034;
(Continued)

(56) References Cited

U.S. PATENT DOCUMENTS

| 2,700,137 A | 1/1955 | Ragan |
| 3,386,069 A | 5/1968 | Eriksson |

(Continued)

FOREIGN PATENT DOCUMENTS

| CN | 103329347 A | 9/2013 |
| EP | 0 073 582 A1 | 8/1982 |

(Continued)

OTHER PUBLICATIONS

British Search Report of related British Patent Application No. GB1518468.2 dated Jul. 1, 2016.
(Continued)

*Primary Examiner* — Tigist S Demie
(74) *Attorney, Agent, or Firm* — ArentFox Schiff LLP

(57) ABSTRACT

Electrical instrument for applying radiofrequency and/or microwave frequency energy to tissue, comprising: a distal part comprising an instrument tip for applying radiofrequency and/or microwave frequency energy to tissue, the instrument tip comprising first and second conductive elements; a coaxial feed cable comprising an inner conductor, a tubular outer conductor coaxial with the inner conductor, and dielectric material separating the inner and outer conductors, the coaxial feed cable being for conveying radiofrequency and/or microwave frequency energy to the distal part; wherein: the inner conductor is electrically connected to the first conductive element and the outer conductor is electrically connected to the second conductive element through a rotatable connection between the distal part and the coaxial feed cable that allows rotation of the distal part (Continued)

relative to the coaxial feed cable; and the instrument comprises an actuator for rotating the distal part in a first rotational direction relative to the feed cable.

6 Claims, 9 Drawing Sheets

(51) Int. Cl.

| | |
|---|---|
| *H01P 1/06* | (2006.01) |
| *A61B 18/12* | (2006.01) |
| *A61B 90/00* | (2016.01) |
| *A61B 18/00* | (2006.01) |
| *H01P 5/08* | (2006.01) |
| *A61B 17/00* | (2006.01) |

(52) U.S. Cl.
CPC .............. *H01P 1/065* (2013.01); *H01P 1/066* (2013.01); *A61B 2017/0034* (2013.01); *A61B 2018/00077* (2013.01); *A61B 2018/00178* (2013.01); *A61B 2018/00202* (2013.01); *A61B 2018/00208* (2013.01); *A61B 2018/00642* (2013.01); *A61B 2018/00755* (2013.01); *A61B 2018/00875* (2013.01); *A61B 2018/00982* (2013.01); *A61B 2018/00994* (2013.01); *A61B 2018/1823* (2013.01); *A61B 2018/1838* (2013.01); *A61B 2018/1861* (2013.01); *A61B 2090/035* (2016.02); *H01P 5/085* (2013.01)

(58) Field of Classification Search
CPC ........... A61B 2018/00077; A61B 2018/00178; A61B 2018/00202; A61B 2018/00208; A61B 2018/00642; A61B 2018/00755; A61B 2018/00875; A61B 2018/00982; A61B 2018/00994; A61B 2018/1823; A61B 2018/1838; A61B 2018/1861; A61B 2090/035
See application file for complete search history.

(56) References Cited

U.S. PATENT DOCUMENTS

| | | | |
|---|---|---|---|
| 5,115,814 A | 5/1992 | Griffith et al. | |
| 5,282,806 A | 2/1994 | Haber et al. | |
| 5,825,958 A * | 10/1998 | Gollihar | A61B 18/22 |
| | | | 385/115 |
| 6,409,728 B1 | 6/2002 | Ehr et al. | |
| 2005/0032421 A1 | 2/2005 | Yamane | |
| 2006/0282069 A1 | 12/2006 | Prakash et al. | |
| 2011/0245827 A1 | 10/2011 | Okada | |
| 2013/0023770 A1 | 1/2013 | Courtney et al. | |
| 2013/0289557 A1* | 10/2013 | Hancock | H01Q 13/08 |
| | | | 606/33 |
| 2015/0012021 A1 | 1/2015 | Mihara | |

FOREIGN PATENT DOCUMENTS

| | | |
|---|---|---|
| EP | 1 013 228 A1 | 6/2000 |
| EP | 2 039 313 A1 | 3/2009 |
| GB | 2474058 A | 4/2011 |
| GB | 2486343 A | 6/2012 |
| GB | 2487199 A | 7/2012 |
| GB | 2503673 A | 1/2014 |
| GB | 2523246 A | 8/2015 |
| JP | 7-61338 B2 | 7/1995 |
| JP | 3179184 B2 | 6/2001 |
| JP | 2005-131173 A | 5/2005 |
| JP | 2010-512214 A | 4/2010 |
| JP | 2010-239995 A | 10/2010 |
| JP | 2012-533379 A | 12/2012 |
| JP | 2014-511190 A | 5/2014 |
| JP | 2015-95821 A | 5/2015 |
| JP | 2015-521873 A | 8/2015 |
| WO | WO 92/16147 A1 | 10/1992 |
| WO | WO 98/16855 A1 | 4/1998 |
| WO | WO 2007/055521 A1 | 5/2007 |

OTHER PUBLICATIONS

British Search Report of related British Patent Application No. GB1518468.2 dated Mar. 17, 2016.
International Search Report of related International Patent Application No. PCT/EP2016/074947 dated May 12, 2017.
The First Office Action from the State Intellectual Property Office of People's Republic of China in counterpart Application No. 201680061159.1, dated Jul. 24, 2020.
Written Opinion of related International Patent Application No. PCT/EP2016/074947 dated Nov. 9, 2017.

* cited by examiner

ELECTROSURGICAL INSTRUMENT

CROSS-REFERENCE TO RELATED APPLICATIONS

This application is a Divisional of U.S. patent application Ser. No. 15/769,685, filed on Apr. 19, 2018, which is a National Stage Entry of International Patent Application No. PCT/EP2016/074947, filed Oct. 18, 2016, which claims priority to United Kingdom Patent Application No. 1518468.2, filed Oct. 19, 2015. The disclosures of the priority applications are incorporated in their entirety herein by reference.

FIELD OF THE INVENTION

The present invention relates to an electrosurgical instrument for applying radiofrequency energy and/or microwave frequency energy to biological tissue. In particular, the present invention relates to such an electrosurgical instrument in which an instrument tip of the instrument is rotatable relative to a coaxial feed cable of the instrument. In practice, the present invention may be passed through an instrument channel of a surgical scoping device, such as an endoscope, gastroscope, neuroscope, laparoscope, etc. Rotation of the instrument tip at the distal end of the endoscope may be controlled at the proximal end of the endoscope.

BACKGROUND OF THE INVENTION

Electrosurgical instruments are instruments that are used to deliver radiofrequency and/or microwave frequency energy to biological tissue, for purposes such as cutting biological tissue or coagulating blood. Radiofrequency and/or microwave frequency energy is supplied to the electrosurgical instrument using a transmission line, such as a coaxial cable, waveguide, microstrip line or the like.

It is know to use coaxial cables to deliver microwave energy along an instrument channel of a surgical scoping device to an electrosurgical instrument at the distal end of that channel. Such coaxial feed cables normally comprise a solid or flexible cylindrical inner conductor, a tubular layer of dielectric material around the inner conductor, and a tubular outer conductor around the dielectric material. The dielectric and/or outer conductor can be multi-layer structures.

An electrical connection is generally formed between the inner and outer conductors of the coaxial feed cable and corresponding conductor elements of an instrument tip (also referred to herein as an end effecter) by soldering a conductor such as a piece of wire or foil to the inner/outer conductor and to the corresponding conductor element. Radiofrequency energy and/or microwave frequency energy can thus be communicated from the coaxial feed cable to the instrument tip for delivery into the biological tissue.

Electrosurgical instruments have been used in conjunction with endoscopes, for example to cut or ablate a small portion of tissue in the gastrointestinal (GI) tract. In this context, the electrosurgical instrument is passed through an instrument channel of the endoscope, so that the instrument tip protrudes from the distal end of the endoscope where it can be brought into contact with the GI tract.

SUMMARY OF THE INVENTION

The present inventors have realised that in some electrosurgical procedures it is advantageous to rotate an instrument tip of an electrosurgical instrument, for example an instrument tip of an electrosurgical instrument that has been passed through the instrument channel of a surgical scoping device. Typically, such an electrosurgical instrument has a flexible shaft that is lies along the length of the instrument channel and terminates at the instrument tip at its distal end. The flexible shaft can be a sleeve that defines a lumen for carrying components of the device, such as a coaxial cable for conveying RF and/or microwave energy, fluid for delivery or cooling at the instrument tip, control lines for actuating movable parts of the instrument tip, etc.

In some cases rotation of the instrument tip can be achieved by rotating the entire electrosurgical instrument around a central axis thereof. However, it can be difficult to control the orientation of the instrument tip when rotating the whole electrosurgical instrument, particularly if the flexible shaft or other components are fixed at the proximal end of the device. For example, rotation of the coaxial cable may be restricted by its connection to an electrosurgical generator.

In practice, friction between the inner surface of the instrument channel and the shaft resists rotation of the shaft, which can cause the shaft to twist along its axis. Accordingly, it may not be possible to achieve 1:1 rotation due to the build up of torque. The resistance experienced by the shaft may increase with length of the device, especially if the tolerances are tight. For example, a 1.8 m long colonoscope with a 2.8 mm diameter instrument channel carrying a shaft having an outer diameter of 2.6 mm. This effect may be more pronounced if the shaft conveys multiple components which give it an irregular cross-sectional shape.

The present inventors have realised there is a need for an electrosurgical instrument in which the rotational orientation of an instrument tip (or end effecter) of the instrument can be controlled independently of the rotational orientation of the flexible shaft.

The present inventors have realised that this can be achieved by providing an electrosurgical instrument in which there is a rotatable connection between a coaxial feed cable and an instrument tip of the instrument (or the end effecter), wherein the rotatable connection allows rotation of the instrument tip relative to the coaxial feed cable while maintaining the necessary electrical connections to enable microwave and RF energy delivery, and by providing means for rotating the instrument tip relative to the coaxial feed cable. The coaxial feed cable may be contained, e.g. fixed within a flexible sleeve. The means for rotating can act to rotate the instrument tip relative to, e.g. around an axis of, the flexible sleeve.

According to a first aspect of the present invention there is provided an electrosurgical instrument for applying radiofrequency energy and/or microwave frequency energy to biological tissue, the instrument comprising: a distal part comprising an instrument tip for applying radiofrequency energy and/or microwave frequency energy to biological tissue, wherein the instrument tip comprises a first conductive element and a second conductive element; a coaxial feed cable comprising an inner conductor, a tubular outer conductor coaxial with the inner conductor, and a dielectric material separating the inner and outer conductors, the coaxial feed cable being for conveying radiofrequency energy and/or microwave frequency energy to the distal part; wherein: the inner conductor is electrically connected to the first conductive element and the outer conductor is electrically connected to the second conductive element through a rotatable connection between the distal part and the coaxial feed cable that allows rotation of the distal part relative to the coaxial feed cable; and the instrument comprises an actuator for rotating the distal part in a first rotational direction relative to the coaxial feed cable With the electrosurgical instrument according to the first aspect of the present invention, the rotational orientation of the instrument tip can be controlled by using the actuator to rotate the distal part (which comprises the instrument tip) relative to the coaxial feed cable. Thus, the rotational orientation of the instrument tip can be precisely and easily controlled, which is advantageous for many types of electrosurgical procedure.

The instrument tip may have any suitable configuration for delivering the RF and/or microwave energy. In an embodiment, the instrument tip may have a fixed geometry, such as a flat spatula or blade, on which the first conductive element and second conductive element are arranged to deliver the RF and/or microwave energy into biological tissue. In another embodiment, the instrument tip may comprise an end effecter having an adjustable geometry. For example, the end effector may be any one of forceps (i.e. a pair of opposed jaws that can open and close), scissors, retractable snare, etc.

A rotatable connection may mean any connection between the coaxial feed cable and the distal part that allows rotation of the distal part relative to the coaxial feed cable while maintaining the electrical connections between the inner conductor and the first conductive element and between the outer conductor and the second conductive element.

Rotation of the distal part means rotation of the distal part around a central axis of the distal part.

Rotation of the distal part relative to the coaxial feed cable means that the distal part can rotate while the coaxial feed cable does not rotate or twist, i.e. while the coaxial feed cable remains stationary.

A rotational direction may mean rotation in either a clockwise of anticlockwise (counter-clockwise) direction.

An electrical connection between two parts means that an electrical signal can be communicated from one of the parts to the other part. It may mean that the two parts are directly connected. Alternatively, it may mean that the two parts are indirectly connected, whereby the electrical signal is communicated between the two parts via a third part.

The inner conductor may be solid. The term solid may mean that the inner conductor is a uniform single piece, for example a single wire. Alternatively, the term solid may mean that the inner conductor is formed from a plurality of wires or fibres arranged or packed together, for example as a braid, to form the inner conductor.

Alternatively, the inner conductor may have a central void or channel, e.g. for conveying other components of the device (e.g. control lines) or for conveying fluid.

In this application, the term distal is used to mean closer to the instrument tip of the electrosurgical instrument than to an opposite end of the electrosurgical instrument where radiofrequency energy and/or microwave frequency energy is input into the electrosurgical instrument. Similarly, the term proximal is used to mean closer to an end of the electrosurgical instrument where radiofrequency energy and/or microwave frequency energy is input into the electrosurgical instrument than to the instrument tip of the electrosurgical instrument. Thus, the instrument tip is at a distal end of the electrosurgical instrument and the radiofrequency energy and/or microwave frequency energy is input into the electrosurgical instrument, e.g. by an electrosurgical generator, at an opposite proximal end of the electrosurgical instrument.

An electrosurgical instrument may be any instrument, or tool, which is used during surgery and which utilises radiofrequency or microwave frequency energy. Herein, radiofrequency (RF) may mean a stable fixed frequency in the range 10 kHz to 300 MHz and microwave energy may mean electromagnetic energy having a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include any one or more of: 915 MHz, 2.45 GHz, 5.8 GHz, 14.5 GHz, 24 GHz.

The electrosurgical instrument may be for cutting, ablating or coagulating tissue or blood, for example.

The electrosurgical instrument according to the first aspect of the present invention may have any one, or, to the extent they are compatible, any combination of the following optional features.

The electrosurgical instrument may be configured for passing through an instrument channel of an endoscope. For example, the width of the coaxial feed cable may be less than an inner diameter of the instrument channel of the endoscope. The width of the instrument tip may also be less than the inner diameter of the instrument channel, so that the electrosurgical instrument can be passed through the instrument channel from the proximal end to the distal end thereof when the endoscope is in situ in the gastrointestinal (GI) tract of a person. The coaxial feed cable may thus have a diameter of less than 3.8 mm, preferably less than 2.8 mm.

Where the electrosurgical instrument is configured for passing through the instrument channel of an endoscope, the actuator preferably enables control of rotation of the instrument tip from a position proximal of the proximal end of the instrument channel, so that an operator of the endoscope can control rotation of the instrument tip at the distal end of the endoscope. The actuator may thus include a control portion at a proximal end of the coaxial feed cable.

The coaxial feed cable is preferably a flexible coaxial feed cable, so that the coaxial feed cable can be passed within a person's GI tract, e.g. in the instrument channel of an endoscope. As discussed above, the coaxial feed cable may be provided within a flexible sleeve. The flexible sleeve may form a protective outer surface for the coaxial feed cable. The outer conductor, dielectric material and inner conductor may be formed on (e.g. as layers inside) the flexible sleeve. In this case, the inner conductor is preferably hollow to form a lumen for other components of the instrument. An inner protective layer may be formed on the inner surface of the hollow inner conductor. Alternatively, the flexible sleeve may itself define a lumen within which a separate coaxial cable (e.g. a Sucoform® cable) is carried. Other components of the instrument, e.g. control lines, etc. may run parallel with the separate coaxial cable. The flexible sleeve may define multiple lumens for carrying respective components.

The distal part may be including a biasing component that resist rotation. Thus, when the distal part is rotated in the first rotational direction relative to the coaxial feed cable, the biasing component acts to rotationally bias the distal part in an opposite second rotational direction. Upon release the distal part may thus be returned to an initial rotational orientation by the rotational bias. This may facilitate operation of the instrument and may also increase the accuracy with which the rotational orientation of the instrument tip can controlled.

The distal part may be rotationally biased towards a predetermined rotational position when the distal part is rotated relative to the coaxial feed cable in the first rotational direction away from the predetermined rotational position.

A predetermined rotational position may mean a predetermined rotational orientation, for example an initial rotational position or orientation.

Rotational biasing of the distal part means that the distal part is biased to rotate around a central axis of the distal part in either a clockwise or anticlockwise (counter-clockwise) direction. In other words, a torque is applied to the distal part that acts to rotate the distal part.

The biasing component (also referred to herein as a biasing element) may be a piece or a part of the instrument that provides the rotational bias. The biasing element may be made under compression, or under tension, or under torsion, or otherwise strained by the rotation of the distal part in the first rotational direction and may thus provide a restoring force that acts to return the distal part to its initial positon. The biasing element may be made of resilient or elastic material.

The biasing element may rotationally bias the distal part towards a predetermined rotational position when the distal part is rotated in the first rotational direction away from the predetermined rotational position.

The biasing element may be a spring or a resilient sleeve. Thus, the spring or resilient sleeve may be placed under compression, or under tension, or under torsion, or otherwise strained by the rotation of the distal part in the first rotational direction.

The resilient sleeve can be a sleeve, sheath or tube that is made of resilient or elastic material, such as silicone. The resilient sleeve may be positioned around the distal part, so that it is under torsion when the distal part is rotated away from the predetermined rotational position.

The spring can be a compression spring, or tension spring, or torsion spring. A helical torsion spring may be particularly suited for storing energy when the distal part is rotated and for providing a biasing force to return the distal part to its initial rotational orientation. A helical torsion spring may be positioned around the distal part, so that the helical torsion spring is under torsion when the distal part is rotated in the first direction away from an initial position.

The biasing element may therefore be considered to be a return spring that acts to return the distal part to an initial rotational orientation when the distal part is rotated away from the initial rotational orientation in the first rotational direction.

The instrument may further comprise a stop element configured to prevent rotation of the distal part in an opposite second rotational direction when the distal part contacts the stop element. Thus, the stop element can prevent the rotational bias from causing the distal part to rotate in the second rotational direction past a particular rotational position, for example an initial starting rotational orientation of the distal part.

A predetermined rotational position towards which the distal part is biased may be the same as an initial starting rotational position of the distal part. Thus, the stop element may be configured to contact the distal part when the distal part is at the predetermined rotational position.

Alternatively, in some embodiments it may be advantageous for the distal part to experience the biasing force when it is in the initial starting rotational position, so that force is required to rotate the distal part away from this position. In this case, the stop element may be configured to contact the distal part at the initial starting rotational position and this may be a different rotational position to a predetermined rotational position towards which the distal part is biased.

The instrument may further comprise a tubular housing in which the coaxial feed cable is received; and the distal part may be rotatably mounted at a distal end of the tubular housing. Thus, the distal part rotates relative to both the coaxial feed cable and the tubular housing. Rotatably mounted may mean that part of the distal part is received in the distal end of the tubular housing and that the distal part is able to rotate relative to the tubular housing. The tubular housing may be part of or mounted on the flexible sleeve mentioned above. A seal may be formed adjacent to the distal end of the tubular housing to prevent ingress of fluid into the tubular housing.

The instrument may comprise an axial stop configured to prevent the distal part from moving axially out of the end of the tubular housing. For example, the distal part may be rotatably received within a ring fixed in the distal end of the tubular housing and a protrusion may be provided on the distal part that contacts an edge of the ring when the distal part is moved axially towards the distal end of the tubular housing, so that the distal part is prevented from being removed from the tubular housing.

The biasing element may be connected to the distal part and to the tubular housing. Thus, the biasing element may be deformed (e.g. made under compression, tension or torsion) when the distal part is rotated within the tubular housing relative to the coaxial feed cable. For example, the biasing element may be connected at a first end thereof to the distal part and at a second end thereof to the tubular housing.

The stop element may be connected to the tubular housing. Thus, the distal part is prevented from rotating relative to the tubular housing in the second direction when the distal part contacts the stop element.

The distal part may comprise a second coaxial feed cable comprising a second inner conductor (which may be solid or hollow), a second tubular outer conductor coaxial with the second inner conductor, and a second dielectric material separating the second inner and outer conductors, the second coaxial feed cable being for conveying radiofrequency energy and/or microwave frequency energy to the instrument tip.

The second inner conductor may be electrically connected to the first conductive element of the instrument tip and the second outer conductor may be electrically connected to the second conductive element of the instrument tip. This electrical connection may be achieved through a conductor such as a conductive wire or conductive foil and a conductive adhesive such as solder. Thus, radiofrequency energy and/or microwave frequency energy can be delivered from the second coaxial feed cable to the instrument tip for delivery to tissue.

The second coaxial feed cable may be connected to the coaxial feed cable by the rotatable connection. Thus, the instrument tip may be rotatable relative to the coaxial feed cable by rotating the second coaxial feed cable relative to the coaxial feed cable. The second inner conductor may be electrically connected to the inner conductor and the second outer conductor may be electrically connected to the outer conductor through the rotatable connection. Thus, radiofrequency energy and/or microwave frequency energy can be delivered to the instrument tip from the coaxial feed cable via the second coaxial feed cable.

A proximal end of the second inner conductor may protrude from a proximal end of the second coaxial feed cable; a distal end of the inner conductor may protrude from a distal end of the coaxial feed cable; and the rotatable connection may comprise: a first conductive part contacting the protruding proximal end of the second inner conductor and the protruding distal end of the inner conductor and forming a rotatable electrical connection therebetween; and a second conductive part contacting a proximal end of the second outer conductor and a distal end of the outer conductor and forming a rotatable electrical connection therebetween.

Thus, the second coaxial feed cable is able to rotate relative to the first coaxial feed cable while maintaining the electrical connections during the rotation.

The second inner conductor and second outer conductor may be able to rotate relative to the conductive parts, and/or the inner conductor and the outer conductor may be able to rotate relative to the conductive parts.

The second inner conductor and second outer conductor may be prevented from moving axially relative to the conductive parts, and/or the inner conductor and outer conductor may be prevented from moving axially relative to the conductive parts, so as to maintain the rotatable electrical connection.

The first conductive part and/or the second conductive part may be a conductive sleeve. In other words, the first conductive part and/or the second conductive part may be a conductive sheath or tube, for example made of metal. The conductive sleeve may surround the ends of the inner/outer conductors and contact the ends of the inner/outer conductor to form the electrical connection.

The conductive sleeve(s) may be an interference fit sleeve(s). This may prevent axial movement of the inner/outer conductors relative to the sleeve(s).

The diameter of the protruding proximal end of the second inner conductor may be different from a main part of the second inner conductor; and the diameter of the protruding distal end of the inner conductor may be different from a main part of the inner conductor. The diameter of the protruding parts may be selected to reduce an impedance mismatch between the coaxial cable or the second coaxial cable and the rotation joint. Depending on the surrounding dielectric, the protruding parts may be wider or narrower than their respective main parts. For example, the coaxial cable and/or the second coaxial cable may have a characteristic impedance of 50Ω and the thickness of the protruding distal end of the inner conductor and/or the protruding proximal end of the second inner conductor may be increased or decreased so that the impedance of the rotational joint is also substantially 50Ω.

The diameter of the protruding proximal end of the second inner conductor may be the same as the diameter of the protruding distal end of the inner conductor; and the diameter of the second outer conductor may be the same as the diameter of the outer conductor. This may reduce any impedance mismatch between the coaxial feed cable and the second coaxial feed cable.

The coaxial feed cable and the second coaxial feed cable may be the same type of coaxial cable and may have the same impedance, for example 50Ω.

In some embodiments, the first conductive part may be fixed to the protruding proximal end of the second inner conductor and to the protruding distal end of the inner conductor; and the first conductive part may be resiliently deformable by rotation of the second coaxial feed cable relative to the coaxial feed cable. Thus, deformation of the first conductive part, i.e. torsion of the first conductive part, when the distal part is rotated relative to the coaxial feed cable may lead to a rotational biasing being applied to the distal part by the first conductive part that acts to return the distal part to an initial rotational configuration in which the first conductive part is not deformed.

In an alternative configuration the rotatable connection may comprise a flexible transmission line. Flexible means that the transmission line can be deformed, for example twisted.

The flexible transmission line may comprise a flexible strip.

The flexible transmission line may be a flexible microstrip transmission line, or a flexible stripline transmission line.

The transmission line may be a substantially planar transmission line when the distal part is in an initial rotational orientation.

The transmission line may be a printed transmission line.

The flexible transmission line may be elastically resilient. Thus, when the flexible transmission line is deformed by rotation of the distal part, the flexible transmission line will provide a biasing force acting to return the distal part to an initial rotational orientation in which the transmission line is not deformed. The flexible transmission line may therefore act as a return spring for returning the distal part to an initial rotational orientation when the distal part is rotated away from the initial rotational orientation. Alternatively, a separate spring as discussed above may be provided to provide the rotational bias.

The flexible transmission line may have a first conductive path electrically connecting the inner conductor to the first conductive element and a second conductive path electrically connecting the outer conductor to the second conductive element.

The conductive paths may be electrically connected to the inner/outer conductor and/or to the first/second conductive elements using a conductive adhesive such as solder (possibly via another conductor, such as a wire or foil).

The flexible transmission line may comprise a flexible microwave substrate.

The flexible transmission line may comprise a flexible microwave substrate having a first conductive path on a first surface thereof and a second conductive path on an opposite second surface thereof; the first conductive path may electrically connect the inner conductor to the first conductive element; and the second conductive path may electrically connect the outer conductor to the second conductive element. Thus, the electrical connections are suitably maintained across the flexible transmission line during rotation of the distal part relative to the coaxial feed cable.

A distal end of the inner conductor may protrude from a distal end of the coaxial feed cable; and the first conductive path may be connected to the protruding distal end of the coaxial feed cable. The connection may be achieved using a conductive adhesive such as solder.

The flexible microwave substrate may comprise a laminate structure comprising two layers laminated together; and the two layers may be delaminated at a distal end of the flexible microwave substrate to form a first layer having the first conductive path and a second layer having the second conductive path. This may be a suitable way of achieving electrical connections to the first and second conductive elements.

The flexible microwave substrate may have a laminate structure comprising two flexible microwave substrate layers laminated together; and the two flexible microwave substrate layers may be delaminated at a distal end of the flexible microwave substrate to form a first flexible microwave substrate having the first conductive path and a second flexible microwave substrate having the second conductive path.

The first conductive path may be connected to the first conductive element on a first surface of the instrument tip; and the second conductive path may be connected to the second conductive element on an opposite second surface of the instrument tip.

The instrument may comprise an actuator element for rotating the distal part relative to the coaxial feed cable; the actuator element may be configured to be moved axially along the instrument; and the distal part may comprise an interface for converting axial movement of the actuator element into rotational movement of the distal part. Thus, the actuator described above may comprise a proximal control portion, an actuator element and an interface. The proximal control portion is accessible by a user and imparts axial movement to the actuator element. The axial movement is transformed by the interface into rotational movement of the distal part. An advantage of this technique for rotating the distal part is that it is possible to precisely control the rotational orientation of the distal part.

The actuator element may be fed down the tubular housing. In other words, the actuator element may extend the whole length of the tubular housing so that it can be operated by an operator at a proximal end of the tubular housing. Where the instrument is passed down an instrument channel of an endoscope, the actuator element may extend at least the whole length of the instrument channel so that it can be operated by an operator at a proximal end of the instrument channel.

The interface for converting axial movement of the actuator element into rotational movement of the distal part may comprise a path on the distal part along which a part of actuator element travels when the actuator element is moved axially, thereby causing the distal part to rotate.

The path may be a raised path, a channel or a groove.

The path may be a helical path or a spiral path about a central axis of the distal part. In other words, the path may curve around at least part of a circumferential surface of the distal part and may extend along at least part of an axial length of the distal part.

The path may be positioned on or around a circumferential surface of the distal part.

The path may be a cam surface of the distal part that makes sliding contact with a part of the actuator element when the actuator element is moved axially, thereby causing the distal part to rotate. Part of a circumferential surface of the distal part may be cut away or omitted to provide the cam surface. For example, a cam channel may be cut away or omitted from the surface of the distal part to provide the cam surface. Thus, when the actuator element is moved axially towards the distal part, the distal part is caused to rotate by the part of the actuator element making sliding contact with the cam surface.

The cam surface may be an edge surface of a raised portion or wall that extends outwardly away from a central axis of the distal part. For example, part of a circumferential surface of the distal part may be cut away or omitted to leave the edge surface.

The instrument may be configured so that the cam surface makes sliding contact with a distal end of the actuator element when the actuator element is moved axially, thereby causing the distal part to rotate. Thus, when the actuator element is moved axially towards the distal part, the distal end of the actuator element contacts the cam surface and forces the distal part to rotate in the first rotational direction so that the distal end of the actuator element follows the cam surface.

The actuator element may be movable in the axial direction (towards the distal part) so that a distal end of the actuator element passes a distal end of the path and protrudes from a distal end of the instrument tip. As discussed below, this may be particularly advantageous where the actuator element is dual purpose, for example where it is a needle for injecting fluid into tissue adjacent the instrument tip.

Once the distal end of the actuator element has passed a distal end of the path, the distal part may remain at its current rotational position until the actuator element is moved axially along the instrument away from the distal end so that the distal end of the actuator element once again contacts the path (or cam surface). When the distal end of the actuator element has passed the distal end of the path, the actuator element may be further displaced axially along the instrument towards the distal part without any further rotation of the instrument tip.

When the distal end of the actuator element passes the distal end of the path (e.g. the cam surface) the actuator element may be positioned adjacent a side surface and/or adjacent a bottom surface of the instrument tip.

While sufficient force is maintained on the actuator element, the biasing is unable to force the distal part to return to its initial rotational orientation. However, when force is removed from the actuator element, the biasing may force the distal part to return to its initial rotational orientation. This may also force the actuator element to return to an original position, for example by forcing the actuator element to move axially away from the distal end.

The actuator element may be for rotating the distal part in a first direction relative to the coaxial feed cable when the actuator element is moved in a first axial direction, and the actuator element may be for rotating the distal part in an opposite second direction relative to the coaxial feed cable when the actuator element is moved in an opposite second axial direction. Thus, rotation of the instrument tip in either of the clockwise and anticlockwise direction can be achieved by moving the actuator element in a forward or backward (first or second) axial direction. In this case, it is not necessary to have any biasing means acting to return the instrument tip to an original rotational orientation, because the instrument tip can be returned to an initial rotational orientation by moving the actuator element axially to an initial axial position.

The actuator element may comprise a helical shaped portion defining a helical path, and the distal part may comprise a follower for causing the distal part to rotatably follow the helical path when the actuator element is moved axially relative to the follower. Thus, as the actuator element is moved axially, the follower rotates to follow the helical path, causing the distal part and therefore the instrument tip to rotate. An axial stop may be provided to prevent any axial movement of the follower, so that the follower is only able to rotate to follow the helical path and cannot be axially displaced by the actuator element.

The follower may comprise a ring having a through-channel in which the helical shaped portion of the actuator element is slidably received. For example, the through channel may be a slot or notch in the circumference of the ring. The shape of the through-channel may be substantially the same as the cross-sectional shape of the helical portion of the actuator element, so that the follower closely follows the helical path as the actuator element is axially displaced.

The follower may be part of a tubular sleeve portion that is fixed to the distal part. For example, the follower may be integral with, or fixed or connected to, the tubular sleeve portion, for example adjacent a proximal end of the sleeve portion. The tubular sleeve portion may be fixed directly to the instrument tip, or to another part of the distal part, such as a skirt portion of the distal part. The tubular sleeve portion rotates together with the distal part, so that rotation of the sleeve portion causes corresponding rotation of the distal part and therefore the instrument tip.

The actuator element may comprise a rod, wire, cable, hollow tube or needle.

The actuator element may comprise a needle for delivering/injecting fluid to biological tissue. Some known electrosurgical instruments use such needles to deliver/inject fluid to biological tissue and therefore it may be advantageous to utilise this needle as the actuator element rather than also providing a separate actuator element. The needle may therefore be dual purpose. Thus, by axially moving the needle along the instrument towards the instrument tip, the needle can be used to change and control the orientation of the instrument tip. Where the distal part is biased, the orientation of the instrument tip can be controlled precisely by moving the needle in either axial direction (forwards or backwards) to achieve clockwise or anticlockwise rotation of the instrument tip. Once the needle has been moved axially to a point where it has passed the axial end of the path, the needle can be moved axially to inject fluid into tissue without affecting the rotational orientation of the instrument tip.

The instrument may also comprise a tubular needle housing for housing the needle. For example, the tubular needle housing may be fed down the tubular housing and the needle may then be fed down the tubular needle housing.

The instrument may comprise a guide part having a guide channel through which the actuator element is fed. The guide part may prevent the actuator element from being moved sideways by the rotational bias that is applied to the distal part. The guide part may constrain the actuator element to only be able to move in an axial direction. For example, where the actuator element is the needle, the needle may be fed through the guide channel directly, or the tubular needle housing containing the needle may be fed through the guide channel.

The guide part may be fixed to the tubular housing. Thus, the actuator element may be constrained to only be able to move in an axial direction relative to the tubular housing. This will prevent the actuator element from moving sideways when it is used to rotate the distal part.

The instrument tip may comprise a planar body made of a dielectric material separating the first conductive element on a first surface thereof from the second conductive element on a second surface thereof, the second surface facing in the opposite direction to the first surface.

The distal part may further comprise a protective hull mounted to cover the underside of the planar body. The protective hull may have a smoothly contoured convex under surface facing away from the planar body; the planar body may have a tapering distal edge; and the underside of the planar body may extend beyond the protective hull at the tapering distal edge.

According to a second aspect of the present invention there is provided electrosurgical instrument for applying radiofrequency energy and/or microwave frequency energy to biological tissue, the instrument comprising: an instrument tip for applying radiofrequency energy and/or microwave frequency energy to biological tissue; a coaxial feed cable for conveying radiofrequency energy and/or microwave frequency energy to the instrument tip; a housing surrounding the coaxial feed cable; and a plurality of bearings positioned between the coaxial feed cable and the housing for enabling rotation of the coaxial feed cable relative to the housing.

Thus, rotation of the instrument tip can be achieved by rotating the whole coaxial feed cable within the housing, which is possible because of the plurality of bearings.

The electrosurgical instrument according to the second aspect of the present invention may have any one, or, to the extent they are compatible, any combination of the following optional features.

The electrosurgical instrument may be configured for passing through an instrument channel of an endoscope. Thus, rotation of the instrument tip at the distal end of the instrument channel can be achieved by rotating the coaxial feed cable at the proximal end of the instrument channel.

The bearings may be any device, component or part that reduce friction between the coaxial feed cable and the housing sufficiently to enable controllable rotation of the coaxial feed cable relative to the housing. For example, the bearings may be rolling element bearings that include rolling elements such as ball bearings, or brush bearings.

There may be only two bearings, one at or close to the distal end of the housing and one at or close to the proximal end of the housing. Alternatively, there may be more than two bearings. Providing additional bearings may help to ensure smooth rotation of the instrument tip, particularly when the housing is bent, by reducing the contact between the coaxial feed cable and the housing.

Other features of the electrosurgical instrument according to the second aspect of the present invention may be the same as the features of the first aspect of the present invention set out above, where compatible.

The electrosurgical instrument according to the first or second aspect of the present invention may have any one, or, where compatible, any combination of the following optional features.

A electrical length of the rotatable section, i.e. the section from the distal end of the coaxial feed cable to the point at which energy is delivered into tissue may be substantially equal to a multiple of $$\frac{\lambda}{2},$$

where $\lambda$ is the wavelength of microwave frequency energy having a predetermined frequency in the instrument tip. The predetermined frequency may be 5.8 GHz. This arrangement effectively makes the transmission line formed by the rotatable section transparent or invisible in terms of mismatch if the insertion loss is negligible. This arrangement may be used as a way of locating the rotatable joint proximally from the instrument tip. For example, the rotatable joint may be position up to 8 cm back from the instrument tip. In this manner it is kept out of the way of the distal end of the scope, where there is often maximum distortion in the instrument channel through manipulation of the scope device and where control lines may be connected.

In another embodiment, a half-wavelength rotation section may be located 6 cm or 8 cm or 10 cm back from the distal end of the instrument and then a quarter wavelength transformer may be disposed at (or integrated into) the distal end of the instrument (e.g. instrument tip or end effecter) to match the impedance of the rotation section to the impedance of the biological tissue at the predetermined frequency.

In another embodiment, a half-wavelength rotation section may disposed at (or integrated into) the distal end of the instrument (e.g. instrument tip or end effecter). This arrangement assumes that the impedance of the biological tissue at the predetermined frequency is the same as the characteristic impedance of the coaxial feed cable. This assumption is reasonable for the delivery of energy at 5.8 GHz into blood using a 50Ω cable.

The distal part may comprise an impedance transformer that substantially matches a characteristic impedance of the coaxial transmission line to a characteristic impedance of a tissue load in contact with the instrument tip at the predetermined frequency.

A length of the impedance transformer may be substantially equal to $$(2n+1)\frac{\lambda}{4},$$

where n is an integer number greater than or equal to zero and λ is the wavelength of the microwave frequency energy in the impedance transformer at the predetermined frequency.

The distal part may further comprise a section of coaxial transmission line between the impedance transformer and a proximal end of the instrument tip.

Alternatively, a characteristic impedance of the instrument tip may be substantially equal to a characteristic impedance of the coaxial feed cable; and the distal part may comprise an impedance matching section for matching the characteristic impedance of the coaxial feed cable to the impedance of a tissue load in contact with the instrument tip at the predetermined frequency of microwave frequency energy, wherein the impedance matching section comprises: a length of coaxial transmission line connected to a proximal end of the instrument tip; and a short circuited stub.

The aspects of the invention discussed above present a rotatable portion for a distal part of an electrosurgical instrument. In some embodiments it may be desirable to provide a plurality of rotatable joints along the length of the coaxial feed cable.

BRIEF DESCRIPTION OF THE DRAWINGS

Embodiments of the present invention will now be discussed, by way of example only, with reference to the accompanying Figures, in which.

DETAILED DESCRIPTION OF THE PREFERRED EMBODIMENTS AND FURTHER OPTIONAL FEATURES OF THE INVENTION

FIGS. 1A to 1D illustrate a method of manufacturing a rotatable connection used in an embodiment of the present invention.

As shown in FIGS. 1A to 1D, a rotatable connection is being formed between a coaxial feed cable 1 and a second coaxial feed cable 3. Each of the coaxial feed cables 1, 3 comprises a solid cylindrical inner conductor, a tubular outer conductor that is coaxial with and surrounds the inner conductor, and a dielectric material separating the inner and outer conductors.

In the embodiment of FIG. 1, the coaxial feed cable 1 and the second coaxial feed cable 3 are the same type of coaxial cable, specifically Sucoform® 047 coaxial cable. In this type of coaxial cable, the inner conductor has an outer diameter of 0.31 mm, the dielectric material layer has an outer diameter of 0.94 mm, and the outer conductor has an outer diameter of 1.2 mm. This type of coaxial cable has a characteristic impedance of 50Ω. The centre conductor is a silver plated copper wire, the dielectric is PTFE and the outer conductor is tin soaked copper braid.

Of course, in other embodiments another type of coaxial cable may be used, and/or the coaxial cable and the second coaxial cable may be different types of coaxial cable with different dimensions and/or characteristic impedances.

Figure 1A:
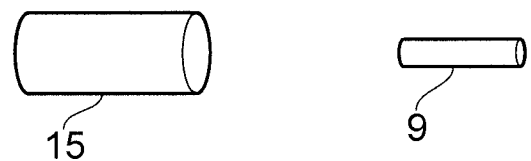
FIGS. 1A to 1D illustrate a method of manufacturing a rotatable connection used in an embodiment of the present invention.
Figure 1B:

As shown in FIG. 1B, a section of the dielectric material and outer conductor of the coaxial feed cable 1 has been omitted or removed to leave a protruding distal end 5 of the inner conductor that protrudes from the distal end of the coaxial feed cable 1. Similarly, a section of the dielectric material and outer conductor of the second coaxial feed cable 3 has been omitted or removed to leave a protruding proximal end 7 of the inner conductor of the second coaxial feed cable (the second inner conductor) that protrudes from the proximal end of the coaxial feed cable 1.

Figure 1C:
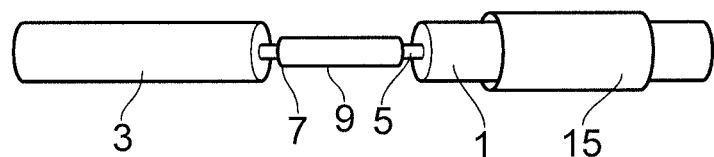

As shown in FIGS. 1A and 1C, a rotatable electrical connection is formed between the inner conductors of the coaxial feed cable 1 and second coaxial feed cable 3 by providing a first conductive metal sleeve 9 over the protruding ends 5, 7 of the inner conductors. The first conductive metal sleeve 9 is a metal tube with a diameter chosen so that the protruding ends 5, 7 of the inner conductors are rotatably received in the metal tube and contact the metal tube to form an electrical connection therebetween. In this embodiment, the first conductive metal sleeve 9 is an interference fit to the protruding ends 5, 7 of the inner conductors.

In this embodiment the first conductive metal sleeve 9 has an outer diameter of 0.59 mm and a length of 2.5 mm. Of course, in other embodiments these dimensions may be different.

Thus, the inner conductor and the second inner conductor are able to rotate relative to each other while an electrical connection is maintained there-between because of the rotatable connection provided by the first conductive metal sleeve 9.

Figure 1D:
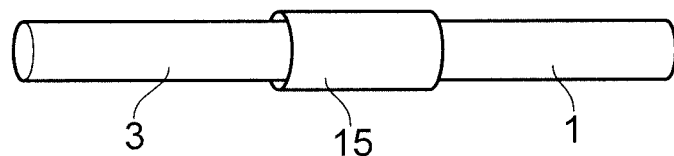

As shown in FIGS. 1A, 1C and 1D, a rotatable electrical connection is formed between the outer conductor 11 of the coaxial feed cable 1 and the outer conductor 13 of the second coaxial feed cable 3 (the second outer conductor) by providing a second conductive metal sleeve 15 over the ends of the outer conductors 11, 13. As shown in FIG. 1C, the second conductive metal sleeve 15 can be positioned over the ends of the outer conductors 11, 13 by sliding it along one of the coaxial feed cables 1, 3 until it is positioned over the ends of the outer conductors 11, 13.

The second conductive metal sleeve 15 is a metal tube with a diameter chosen so that the ends of the outer conductors 11, 13 are rotatably received in the metal tube and contact the metal tube to form an electrical connection therebetween. In this embodiment, the second conductive metal sleeve 15 is an interference fit to the ends of the outer conductors 11, 13.

In this embodiment the second conductive metal sleeve 15 has an inner diameter of 1.15 mm. Of course, in other embodiments the diameter may be different.

Thus, the outer conductors 11, 13 of the coaxial feed cable 1 and the second coaxial feed cable 3 are able to rotate relative to each other while an electrical connection is maintained there-between because of the rotatable connection provided by the second conductive metal sleeve 15.

Thus, the combination of the first and second conductive metal sleeves 11, 13 provides a rotatable connection between the coaxial feed cable 1 and the second coaxial feed cable 3 that allows the second coaxial feed cable 3 to be rotated relative to the coaxial feed cable 1, while maintaining an electrical connection between the coaxial feed cable 1 and the second coaxial feed cable 3.

Radiofrequency energy and/or microwave frequency energy can be transmitted from the coaxial feed cable 1 to the second coaxial feed cable 3 through the rotatable connection because of the rotatable electrical connections provided by the first and second conductive metal sleeves 9, 15.

The first and second conductive metal sleeves 9, 15 form a coaxial transmission line for conveying the radiofrequency energy and/or microwave energy with air as the dielectric material. In other embodiments a dielectric filler material may be provided between the first and second conductive metal sleeves 9, 15

In an embodiment of the present invention, the second coaxial feed cable 3 may be connected to an instrument tip and may convey radiofrequency energy and/or microwave frequency energy from the coaxial feed cable 1 to the instrument tip. For example, the instrument tip may have a first conductive element electrically connected to the second inner conductor and a second conductive element electrically connected to the second outer conductor. Thus, the instrument tip is rotatable relative to the coaxial feed cable 1 by the rotatable connection. The electrical connections may be achieved with electrical conductors such as conductive wires or sheets that are connected to the conductive elements of the instrument tip and to the conductors by conductive adhesive, such as solder.

The coaxial feed cable 1 may have a connector at a proximal end thereof for connecting the coaxial feed cable 1 to an electrosurgical generator for supplying the radiofrequency energy and/or microwave frequency energy. For example, the connector may be a conventional coaxial cable end connector.

Having air as the dielectric material between the first and second conductive metal sleeves 9, 15 as in FIG. 1 will increase the characteristic impedance of the rotational joint relative to the impedance(s) of the coaxial feed cables 1, 3. The impedance mismatch between the coaxial feed cables 1, 3 and the rotational joint will lead to reflection of some of the radiofrequency energy and/or microwave frequency energy. Therefore, in one embodiment the protruding ends 5, 7 of the inner conductors may have an increased diameter, and the first conductive metal sleeve 9 may have a correspondingly larger internal diameter. Thus, the impedance of the rotational joint will be decreased, so that it is closer to the impedance of the coaxial feed cables 1, 4. Ideally, the impedance of the rotational joint would be the same as the impedance of the coaxial feed cables, for example 50 Ohms.

The electrical properties of the rotational joint illustrated in FIGS. 1A to 1D are now described.

The characteristic impedance $Z_0$ of a coaxial transmission line is approximately given by equation (1).

$$Z_0 \cong 138 \sqrt{\frac{\mu_r}{\varepsilon_r}} \log_{10} \frac{b}{a} \tag{1}$$

Where $\mu_r$ is the relative permeability of the dielectric material, $\varepsilon_r$ is the relative permittivity of the dielectric material, b is the inner diameter of the outer conductor and a is the outer diameter of the inner conductor. The ratio $$\frac{b}{a}$$

may be obtained using the respective radii of the outer conductor and inner conductor.

The attenuation of the radiofrequency energy and/or microwave frequency energy because of the rotational joint is given in equation (2).

$$\alpha_T = \alpha_c + \alpha_d \tag{2}$$

Where $\alpha_T$ is the total attenuation of the rotational joint, $\alpha_c$ is the attenuation due to the first and second conductive metal sleeves 9, 15 in the rotational joint and $\alpha_d$ is the attenuation due to the dielectric (air in FIG. 1) in the rotational joint.

The attenuation due to the conductor is given in equation (3).

$$\alpha_c = 13.6 \frac{\delta_s \sqrt{\varepsilon_r}\left(1+\frac{b}{a}\right)}{\lambda_0 \times b \times \ln\frac{b}{a}} dB/m \tag{3}$$

Where $\delta_s$ is the skin depth of the radiofrequency energy and/or microwave frequency energy within the first and second conductive metal sleeves 9, 15, $\varepsilon_r$ is the relative permittivity, $\lambda_0$ is the free space wavelength, b is the inner diameter of the outer conductor and a is the outer diameter of the inner conductor.

The attenuation due to the dielectric is given in equation (4)

$$\alpha_d = 27.3 \frac{\sqrt{\varepsilon_r}}{\lambda_0} \tan\delta \text{ dB/m} \qquad (4)$$

In the embodiment illustrated in FIG. 1, the first conductive metal sleeve 9 has an outer diameter of 0.59 mm and a length of 2.5 mm. The second conductive metal sleeve 15 has an inner diameter of 1.15 mm.

With air as the dielectric material between the first and second conductive metal sleeves 9, 15 the impedance and attenuation due to the conductors of the rotational joint are given in equations (5) and (6).

$$Z_0 = 138\sqrt{\frac{1}{1.00059}} \log\frac{0.575}{0.295} = 39.88 \text{ }\Omega \qquad (5)$$

$$\alpha_c = 13.6 \frac{(0.86 \times 10^{-6})\sqrt{1}\left(1 + \frac{0.575}{0.295}\right)}{0.0517 \times 0.575 \times \text{Ln}\frac{0.575}{0.295}} = 1.738 \text{ dB/m} \qquad (6)$$

Assuming that the air filled rotational joint has tan $\delta$=0, the attenuation due to the dielectric is given in equation (7).

$$\alpha_d = 27.3 \frac{\sqrt{1.00059}}{0.0517} \times 0 = 0 \qquad (7)$$

Relating these equations to the specific length of the first conductive metal sleeve 9 of 2.5 mm in this particular embodiment leads to equation (8).

$$\alpha = \alpha_c + \alpha_d = 1.738 \text{ dB/m} \qquad (8)$$

$$\alpha = \frac{1.738 \text{ dB}}{\text{m}} \times 0.0025 \text{ m} = 0.004346 \text{ dB}$$

Equation (8) gives the associated loss within the 2.5 mm length rotating sleeve section. This calculation does not take into account any small impedance mismatch between the characteristic line impedance and the rotating joint. The slight mismatch will increase insertion loss due to increased reflection, but in testing it has been found that this increase is negligible.

A layer of insulation may be provided between the first and second conductive metal sleeves 9, 15 to prevent electrical breakdown of the air between the metal sleeves 9, 15 during radiofrequency energy operation of the instrument. For example, the insulation may be Kapton tape or PTFE.

In one embodiment, the first conductive metal sleeve 9 may be fixed to the protruding ends 5, 7 of the inner conductors. The first conductive metal sleeve 9 may be made of a resiliently deformable material, so that the first conductive metal sleeve 9 is resiliently deformed (e.g. twisted under torsion) when the second coaxial feed cable 3 is rotated relative to the coaxial feed cable 1. Thus, the first conductive metal sleeve 9 may provide a rotational biasing force on the second coaxial feed cable 3 causing it to return to an initial rotational orientation in which the first conductive metal sleeve 9 is not deformed. Thus, the first conductive metal sleeve 9 may act as a return spring.

Of course, in other embodiments of the present invention a different type of rotatable connection may be provided. Many different types of such rotatable connection are possible. Specific methods for controlling the rotation of an electrosurgical instrument at the distal end of the arrangements illustrated in FIGS. 1A to 1D are discussed below.

Figure 2A:
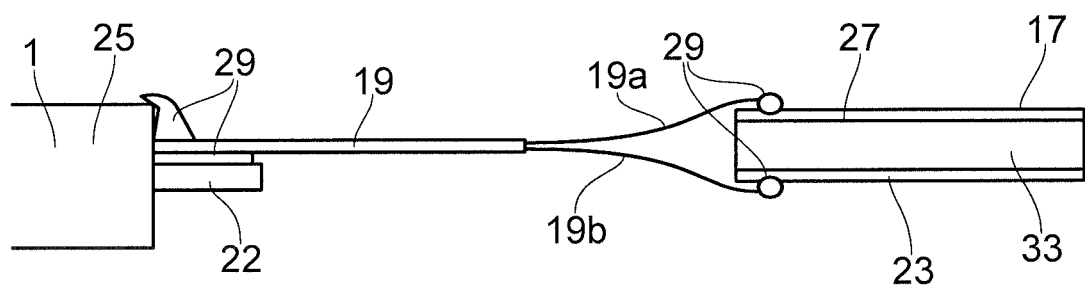
FIGS. 2A and 2B illustrate a further rotatable connection used in a further embodiment of the present invention.
Figure 2B:
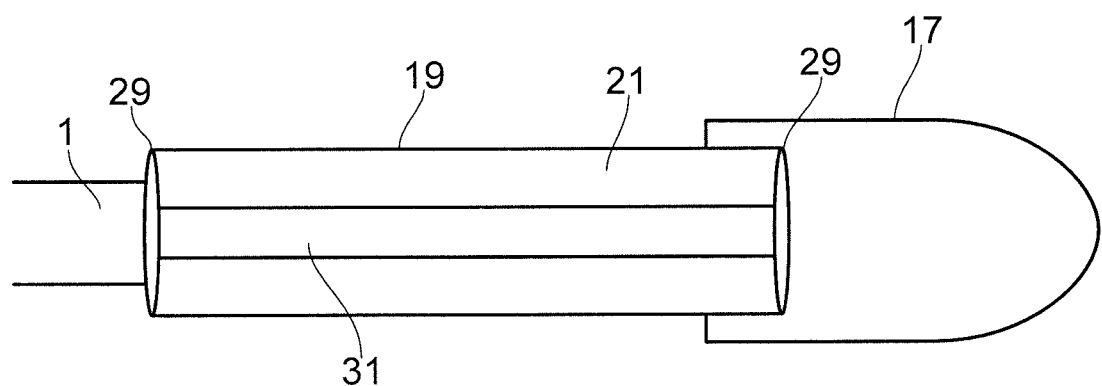

FIGS. 2A and 2B illustrate a further rotatable connection used in a further embodiment of the present invention.

As illustrated in FIGS. 2A and 2B, in this embodiment the coaxial feed cable 1 is connected to an electrosurgical instrument tip 17 by a flexible transmission line 19. Flexible means that the transmission line can be deformed, for example twisted or bent, without being broken or permanently damaged. For example, it can be twisted under torsion.

The flexible transmission line 19 comprises a flexible microwave substrate 21. For example, the flexible microwave substrate 21 might be RFlex microwave substrate from Rogers Corporation.

The flexible transmission line 19 electrically connects the inner conductor 22 of the coaxial feed cable 1 to a first conductive element 23 on an underside of the instrument tip 17 and also electrically connects the outer conductor 25 to a second conductive element 27 on an (opposite) upper side of the instrument tip 17. Thus, the flexible transmission line 19 is configured to convey radiofrequency energy and/or microwave frequency energy from the coaxial feed cable 1 to the first and second conductive elements 23, 27 of the instrument tip 17, for delivery into tissue in contact with the instrument tip 17.

The electrical connection between the inner conductor 22 and the first conductive element 23 is achieved by a first conductive path formed along the length of the flexible transmission line 19 that is electrically connected to the inner conductor 21 and to the first conductive element 23 by a conductive adhesive such as solder 29. The first conductive path may be formed of metal, and may be printed on a surface of the flexible microwave substrate 21, for example on an underside of the flexible microwave substrate 21.

Similarly, the electrical connection between the outer conductor 25 and the second conductive element 27 is achieved by a second conductive path 31 formed along the length of the flexible transmission line 19 that is electrically connected to the outer conductor 25 and to the second conductive element 27 by a conductive adhesive such as solder 29. The second conductive path 31 may be formed of metal, and may be printed on the opposite surface of the flexible microwave substrate 21, for example on an upper side of the flexible microwave substrate.

In this embodiment, the instrument tip 17 comprises a planar body made of a dielectric material 33 separating the first conductive element 23 on a first surface thereof from the second conductive element 27 on a second surface thereof, the second surface facing in the opposite direction to the first surface.

The first and second conductive paths may be made of copper. The first and second conductive paths may be printed on the flexible transmission line.

In the embodiment shown in FIGS. 2A and 2B, the flexible transmission line 19 is split into two parts 19a, 19b adjacent to the instrument tip 17. The first part 19a has the second conductive path 31 on an upper surface thereof and the second part 19b has the first conductive path on a bottom surface thereof. Splitting of the flexible transmission line 19 may be achieved by using a laminated flexible transmission line 19 that comprises two layers of material laminated together, and delaminating the two layers of material adjacent to the instrument tip 17 to split the flexible transmission line 19 into two parts as illustrated in FIG. 2.

However, in other embodiments, the flexible transmission line 19 does not divide in this manner. Instead additional connector portions may be provided to connect the conductive paths on the flexible substrate to their respective terminals on the instrument tip.

In this embodiment the flexible transmission line 19 is substantially planar and substantially flat when in an initial (non-twisted) configuration. The flexible transmission line is in the form of a flexible (twistable) strip.

Since the flexible transmission line 19 is flexible, if the instrument tip 17 is rotated relative to the coaxial feed cable 1, the flexible transmission line 19 allows the rotation by deforming. Specifically, the flexible transmission line 19 will be under torsion and will twist when the instrument tip 17 is rotated relative to the coaxial feed cable 1. Thus, the flexible transmission line 19 constitutes a rotatable connection between the coaxial feed cable 1 and the instrument tip 17 that allows rotation of the instrument tip 17 relative to the coaxial feed cable 1, while maintaining the electrical connections between the inner/outer conductors 22, 25 of the coaxial feed cable 1 and the first/second conductive elements 23, 27 of the instrument tip 17. Radiofrequency energy and/or microwave frequency energy can thus be conveyed from the coaxial feed cable 1 to the instrument tip 17 via the flexible transmission line 19 during rotation of the instrument tip 17 relative to the coaxial feed cable.

The flexible transmission line 19 may be elastically resilient. In other words, when the flexible transmission line is deformed by twisting of the flexible transmission line 19, it may provide a biasing force to return the flexible transmission line to an original (e.g. flat) orientation. Thus, the flexible transmission line 19 may also function as a return spring for returning the instrument tip 17 to an initial rotational position in which the transmission line is substantially flat when the instrument tip 17 is rotated away from the initial position.

The flexible transmission line 19 may have a coating, covering, or other seal to prevent liquid from coming into contact with the electrical connections or paths. For example, the flexible transmission line 19 may comprise a layer or coating of insulating material, such as a rubber material or polymer, on one or more surface thereof, to prevent liquid from coming into contact with an electrical connection or path of the flexible transmission line 19. Alternatively, seals may be provided adjacent to each axial end of the flexible transmission line 19 to prevent liquid from coming into contact with the flexible transmission line 19.

In some embodiments, the flexible transmission line may be a flexible microstrip. In such embodiments, the flexible transmission line comprises a planar conducting strip separated from a ground plane by a substrate dielectric layer. The microstrip may be fabricated using printed circuit board technology. The ground plane and planar conducting strip may each be electrically connected to a respective one of the first and second conductive elements of the instrument tip. In such embodiments, the planar conducting strip and ground plane may be prevented from coming into contact with liquid by a coating, covering or other seal as described above. As described above, the substrate dielectric layer may be a laminate structure which can be split adjacent to the instrument tip to allow electrical connection of the flexible microstrip to conductive elements on opposite surfaces of the instrument tip.

In alternative embodiments the flexible transmission line may be a flexible stripline. In such embodiments, the flexible transmission line comprises a central conductor formed within a substrate dielectric layer that is sandwiched between ground planes on opposite sides of the substrate dielectric layer. Such an arrangement has an advantage that the central conductor is prevented from coming into contact with liquid because it is surrounded by the dielectric layer, so it may not be necessary to provide any further barriers to prevent liquid coming into contact with the flexible transmission line. With this structure, when forming the electrical connection to the instrument tip, the ground planes can be terminated a predetermined distance before the distal end of the flexible transmission line.

In the embodiment illustrated in FIGS. 2A and 2B, the flexible transmission line 19 directly connects the coaxial feed cable 1 to the instrument tip 17. However, this is not essential. For example, the flexible transmission line 19 may be set back from the instrument tip and a further coaxial transmission line may be provided between the flexible transmission line 19 and the instrument tip 17, to space the flexible transmission line 19 from the other parts at the distal end of the cable arrangement. However, it is advantageous to have the flexible transmission line 19 close to the instrument tip 17 to enable suitable control of the rotation of the instrument tip 17. Furthermore, in embodiments where the instrument tip 17 has a planar structure, for example as shown in FIGS. 2A and 2B, it is advantageous for the flexible transmission line 19 to directly connect the coaxial feed cable 1 to the instrument tip 17, because the flexible transmission line 19 converts the round/cylindrical structure of the coaxial feed cable 1 to the flat/planar structure of the instrument tip 17.

Of course, in other embodiments the flexible transmission line may be different to that shown in FIGS. 2A and 2B or described above. The important feature is that the flexible transmission line provides the necessary electrical connections and allows rotation of the instrument tip relative to the coaxial feed cable.

In other embodiments a different type of rotatable connection may be provided between the coaxial feed cable 1 and the instrument tip to those illustrated in FIGS. 1A to 2B. The important feature is that the rotatable connection provides the necessary electrical connections and allows rotation of the instrument tip relative to the coaxial feed cable.

Mechanisms for causing rotation of an instrument tip relative to a coaxial feed cable and mechanisms for providing a rotational bias to the instrument tip will now be discussed. Although the rotation and biasing mechanisms are combined together in the embodiment described below, other embodiments of the present invention may have only one of these specific mechanisms, e.g. just the rotation mechanism or just the biasing mechanism.

FIGS. 3A to 5 show various configurations of a model of an electrosurgical instrument 35 according to an embodiment of the present invention. As shown in FIGS. 3A to 5, the instrument 35 comprises an instrument tip 37 and a coaxial feed cable 39 that is fixed to the instrument tip 37. In practice, the instrument tip 37 will comprise first and second conductive elements for delivering radiofrequency energy and/or microwave frequency energy into biological tissue in contact with the instrument tip 37. For example, the instrument tip may have a structure similar to that of the instrument tip illustrated in FIG. 2A.

In practice, the coaxial feed cable 39 is fixed to the instrument tip 37 by an inner conductor of the coaxial feed cable 39 being fixed by conductive adhesive such as solder to a first of the conductive elements of the instrument tip 37, and by an outer conductor of the coaxial feed cable 39 being fixed by conductive adhesive such as solder to a second of the conductive elements (possibly via additional conductors such as wire or foil).

Thus, the instrument tip 37 cannot rotate relative to the coaxial feed cable 39.

Figure 5:
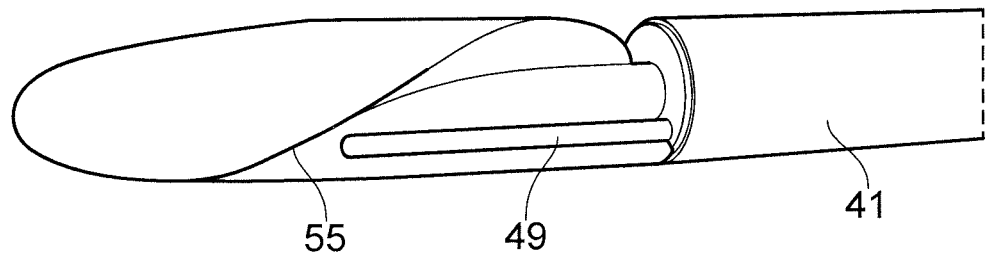

The coaxial feed cable 39 (or at least some of the coaxial feed cable 39) is received within a tubular housing 41. For example, the tubular housing 41 may be a flexible plastic or polymer tube. The coaxial feed cable 39 may be fed along the tubular housing 41. The coaxial feed cable 39 is able to rotate relative to the tubular housing 41. In other words, the coaxial feed cable 39 is not fixed relative to the tubular housing 41. In FIG. 5 the tubular housing 41 is shown as being opaque, which it is likely to be in practice.

The instrument tip 37 is rotatably mounted at a distal end of the tubular housing 41. In other words, part of the instrument tip 37 is received in the distal end of the tubular housing 41 and can rotate relative to the tubular housing 41. This may be achieved by the instrument tip 37 having a shaft or a shank portion at the proximal end thereof that is shaped to be received in the distal end of the tubular housing so that is can rotate therein. Alternatively, a tubular part may be fixed around an outside of part of a shaft or shank portion of the instrument tip, wherein the tubular part is received within the distal end of the tubular housing 41 and can rotate relative to the tubular housing 41.

Thus, both the instrument tip 37 and the coaxial feed cable 39 form a distal part of the instrument 35 that is able to rotate relative to the tubular housing 41.

Figure 3A:
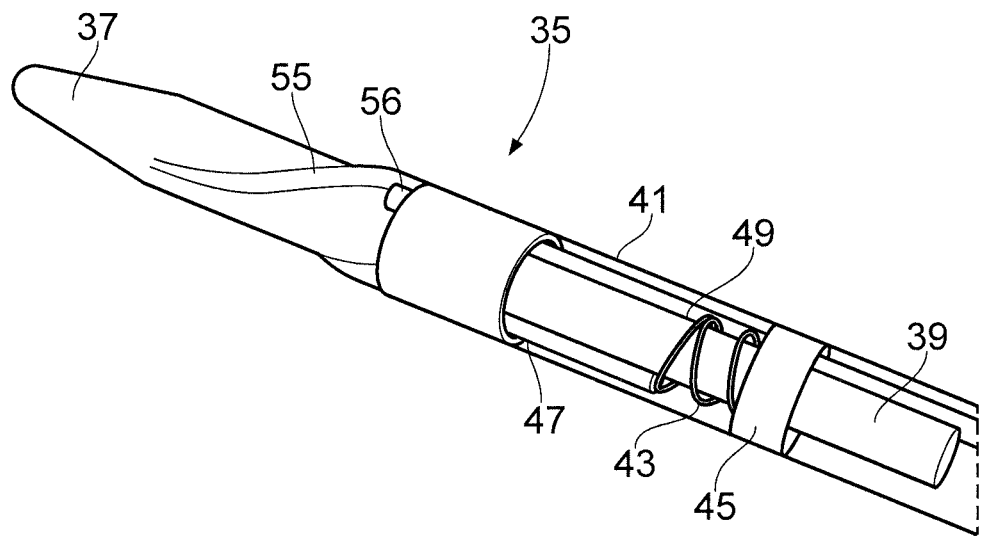
FIGS. 3A and 3B show various configurations of a working model of an electrosurgical instrument according to an embodiment of the present invention.

A stop part may be provided on the instrument tip 37, or in the distal end of the tubular housing 41, to prevent the instrument tip from moving axially out of the distal end of the tubular housing. A seal may also be provided on a part of the instrument tip 37, to prevent the ingress of fluid into the tubular housing 41. For example, a seal may be provided on or around a part of a shaft or shank portion of the instrument tip 37 that is received in the tubular housing 41, As shown in FIGS. 3A to 4, a spring 43 is also provided in the tubular housing 41. The spring 43 is a helical torsion spring that is positioned around the outside of the coaxial feed cable 39.

A first end of the spring 43 is fixed to the tubular housing 41. In this embodiment, the first end of the spring 43 is fixed to the tubular housing 41 by being fixed to a ring part 45 that is fixed to an internal surface of the tubular housing 41. A second end of the spring 43 is fixed to the distal part of the instrument 35. Specifically, the second end of the spring is connected to a skirt portion 47 that extends axially from the instrument tip 37 towards the proximal end of the instrument 35. The skirt portion 47 is integral with the instrument tip 37 and rotates together with the instrument tip 37.

Thus, if the distal part of the instrument 35 comprising the instrument tip 37, skirt portion 47 and coaxial feed cable 39 is rotated within the tubular housing 41 towards the right in FIG. 3A, the helical torsion spring 43 is twisted because its second end rotates with the distal part whereas its first end is fixed to the tubular housing 41. Thus, mechanical energy is stored in the helical torsion spring 43. This stored mechanical energy causes the helical torsion spring 43 to exert a rotational biasing force on the distal part that biases the distal part to rotate in the opposite direction, i.e. towards the left in FIG. 3A.

Thus, the helical torsion spring 43 functions as a reset spring that provides a force for resetting the distal part to an initial rotational position/orientation when the distal part is rotated away from that rotational position/orientation.

In practice, the coaxial feed cable 39 will be connected to a further coaxial feed cable by a rotatable connection such as that illustrated in FIGS. 1A to 1D and described above, so that radiofrequency energy and/or microwave frequency energy can be conveyed to the coaxial feed cable 39 (and therefore to the instrument tip 37) from the further coaxial feed cable and so that the coaxial feed cable 39 (and therefore the distal part of the instrument 35) can rotate relative to the further coaxial feed cable. In practice the further coaxial feed cable will be connected to an electrosurgical generator for generating and supplying the radiofrequency energy and/or microwave frequency energy.

The instrument comprises a stop element configured to prevent rotation of the distal part in a particular rotational direction (to the left in FIG. 3A) when the distal part contacts the stop element. Thus, the stop element can prevent the rotational bias from causing the distal part to rotate in the particular rotational direction beyond a particular rotational position, for example an initial starting rotational orientation of the distal part. The stop element and/or the spring 43 may be configured so that the spring 43 applies a bias force to the distal part when the distal part is in an initial position in contact with the stop element. Thus, in order to rotate the distal part away from the initial position force must be applied to overcome the rotational bias.

Of course, a similar biasing method to that illustrated in FIG. 3A may be used with other types of rotatable connection between the instrument tip and the main coaxial feed cable (the coaxial feed cable that is normally connected to an electrosurgical generator). For example, the coaxial feed cable 39 in FIG. 3A could be replaced with a flexible transmission line, for example as illustrated in FIGS. 2A and 2B and described above, which is connected (preferably fixed) to the main coaxial feed cable. The helical torsion spring 43 could then be positioned around the flexible transmission line, or around another part of the distal part of the instrument 35, so that the same biasing effect is achieved when the instrument tip is rotated and the flexible transmission line is twisted.

Alternatively, in other embodiments the biasing force may be provided by part of the rotatable connection, as discussed above in relation to FIGS. 1A to 2B (for example by the flexible transmission line being elastically resilient), and therefore the spring 43 in FIG. 3A may be omitted in these embodiments (this configuration is discussed in more detail below in reference to FIG. 9).

The biasing force may be provided by another resilient element, such as a resilient sleeve, instead of by the spring 43.

Of course, in yet further embodiments there may be no need or desire for a rotational bias force on the instrument tip at all, and therefore the spring 43 in FIG. 3A may also be omitted in these embodiments. Such an embodiment is discussed below in relation to FIGS. 10 and 11.

A mechanism for rotating the instrument tip 37 will now be described.

In FIG. 3A, the instrument tip 37 is rotated using an actuator element 49 in the form of a rod 49 that is fed down the tubular housing 41 and that can be moved axially along the tubular housing 41 by an operator of the instrument 35. As discussed below, in some embodiments the rod 49 may be a needle of the instrument for injecting fluid such as saline into tissue adjacent the instrument tip.

Figure 3B:
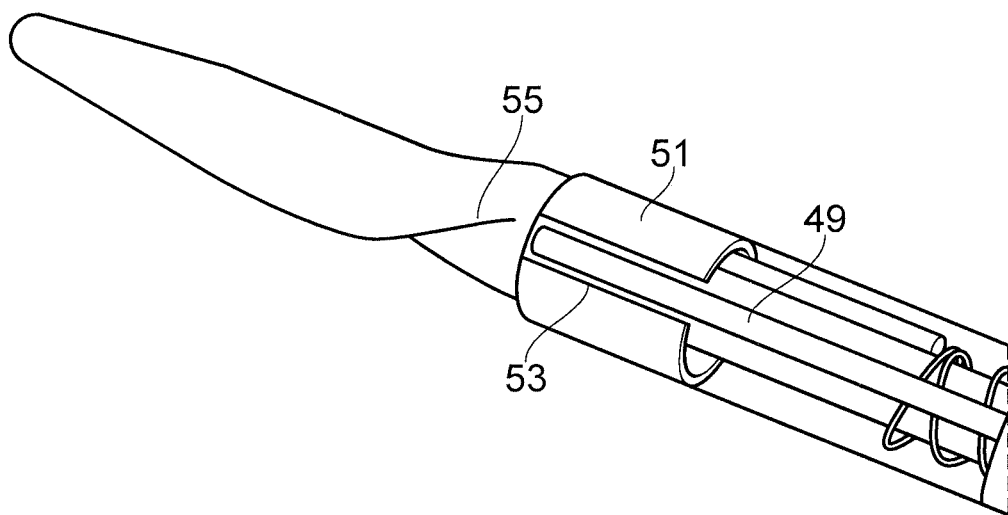
Figure 4:
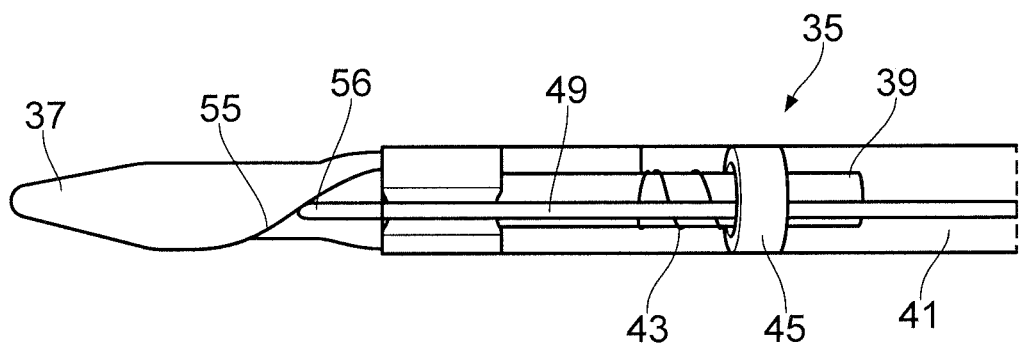
FIGS. 4 and 5 show various configurations of a working model of an electrosurgical instrument according to an embodiment of the present invention.

As best seen in FIG. 3B, the instrument comprises a guide part 51 having a guide channel 53 through which the actuator element 49 is fed. The guide part 51 prevents the actuator element 49 from being moved sideways by the rotational bias that is applied to the distal part. Specifically, the guide part 51 constrains movement of the actuator element 49 so that it can only move in the axial direction relative to the guide part 51. In this embodiment, the guide part 51 is a ring fixed to an internal surface of the tubular housing 41 and surrounding the coaxial feed cable 39. As shown in FIG. 3B, the ring has an axial guide channel 53 through which the actuator element 49 is fed. Thus, the actuator element 49 is able to move axially relative to the ring but cannot move sideways because it is constrained to remain within the guide channel 53.

The axial guide channel 53 may comprise a segment of the ring that is omitted or cut away (so that is it not a complete ring) or a bore or channel formed in, or through, the ring.

The rotatable distal part of the instrument 35 comprises an interface for converting axial movement of the actuator element 49 into rotational movement of the distal part.

In this embodiment, the interface comprises a cam surface of the instrument tip. The cam surface is a raised helical edge 55 (or spiral edge) that extends in a helical (or spiral) manner around at least part of an outer surface of the instrument tip 37 and along at least part of the length of the instrument tip. The helical edge 55 may be formed by cutting away or omitting a suitably shaped portion of the outer surface of the instrument tip 37 (e.g. to form a cam channel).

The raised helical edge 55 is configured so that it is contacted by a distal end 56 of the actuator element 49 as the actuator element 49 is moved axially along the instrument 35 towards the instrument tip 37, so that the distal end of the actuator element 49 slides along the raised helical edge 55 and forces the instrument tip 37 to rotate.

In some embodiments the helical edge 55 may have a curved surface, like a channel or groove, to better cooperate (e.g. receive or engage) with the distal end of the actuator element 49.

As the actuator element 49 is moved axially along the instrument 35, the distal end 56 of the actuator element 49 contacts the raised helical edge 55 on the instrument tip 37. The actuator element 49 is only free to move in the axial direction because of the guide part 51. The instrument tip 37 is prevented from moving axially, for example by a further stop part that prevents axial movement of the instrument tip 37, but is free to rotate within the tubular housing 41. Thus, the action of the distal end of the actuator element 49 contacting and applying force to the raised helical edge 55 causes the raised helical edge 55 to be displaced sideways, so that the actuator element 49 continues to move axially and to slide along the raised helical edge 55 so that the instrument tip 37 starts to rotate. In FIG. 3A the instrument tip will rotate to the right (clockwise from the point of view of the proximal end of the instrument 35) as the actuator element 49 is progressively moved axially towards the instrument tip 37.

Where the instrument tip 37 is biased towards the initial position as discussed above, the rotation of the instrument tip 37 is against the rotational bias and leads to energy being stored in the biasing element (e.g. spring 43). Thus, a force needs to be maintained on the actuator element 49 to overcome the rotational bias to keep rotating the instrument tip 37, otherwise the rotation bias will act to return the instrument tip 37 to its initial rotational orientation and consequently the actuator element 49 will be displaced axially back along the instrument by the rotation of the raised helical edge 55.

Rotation of the instrument tip 37 continues with progressive axial displacement of the actuator element 49 until the distal end of the actuator element 49 passes a distal end of the raised helical edge 55. From then on, further axial movement of the actuator element 49 towards the instrument tip 37 does not cause any further rotation of the instrument tip 37. Where the instrument tip 37 is rotationally biased towards its initial position, the raised helical edge 55 acting on the shaft of the actuator element 49, which is unable to move sideways because the guide part 55 prevents the rotational bias from causing the instrument tip 37 to rotate. Thus, the rotational bias is unable to rotate the instrument tip 37 back to its initial rotational orientation until the actuator element 49 is retracted to the point where its distal tip is again in contact with the raised helical edge 55.

The actuator element 49 may comprise a needle of the instrument 35 that is used for injecting fluid, such as saline, into biological tissue in contact with the instrument tip 37. In known electrosurgical instruments such needles have been provided by being fed down a tube within the tubular housing. Such needles are capable of being moved axially along the tubular housing, for example to extend or retract a needle tip of the needle at the distal end of the instrument. Thus, the distal end of the needle can be used to contact the helical path (cam surface) of the instrument tip as described above, so that axial movement of the needle can be used to cause rotation of the instrument tip. Utilising the existing needle component of the electrosurgical instrument in this dual-purpose manner removes the need to provide a further actuator element 49, and therefore results in a simpler and more efficient electrosurgical instrument. The orientation of the instrument tip may be unimportant during the injecting process using the needle. The injection may be performed first, and then the orientation of the instrument tip may be controlled during electrosurgery by subsequently retracting the needle to a point where the tip of the needle contacts the cam surface of the instrument tip. Alternatively, the injection may be carried out after controlling the rotational orientation of the instrument tip during electrosurgery.

Once the distal end of the needle has passed a distal end of the cam surface, further axial movement of the needle to inject fluid into the tissue will not affect the orientation of the instrument tip. After being used for injecting fluid into the tissue, the needle can be retracted until its tip is in contact with the cam surface (raised helical edge 55), and the needle can then be moved in either axial direction to control clockwise and anticlockwise rotation of the instrument tip 37.

In one embodiment, the helical path (cam surface) is configured (e.g. its position and/or length and/or pitch are set) so that when the distal end of the actuator element passes the distal end of the helical path the instrument tip is oriented with the actuator element positioned adjacent a side surface and/or a bottom surface of the instrument tip. This may be an advantageous position for the actuator element to be positioned, particularly where the actuator element is a needle of the instrument as described above.

When the actuator element 49 is retracted progressively back along the instrument 35, the biasing force pressing the raised helical edge 55 into contact with the distal end of the actuator element 49 causes the instrument tip 37 to progressively rotate, in the opposite direction to before, back towards its initial orientation. Thus, the rotational orientation of the instrument tip 37 can be easily and accurately controlled and returned to its initial position when the actuator element 49 is retracted.

Of course, the same rotation actuation mechanism described above can be used with different types of rotatable connection, for example with the flexible transmission line rotatable connection illustrated in FIGS. 2A and 2B and described above (this configuration is discussed below in reference to FIG. 7). Furthermore, the rotation actuation mechanism described above can be used with other types of rotational biasing.

In some embodiments it may be unnecessary to provide the rotational bias to return the instrument tip to its initial rotational orientation. Instead, the interaction between the actuator element and the instrument tip may be such that axial movement of the actuator element away from the instrument tip causes the instrument tip to rotate, in the opposite direction to before, back towards its initial rotational orientation. For example, the actuator element may comprise a follower in the form of a protrusion that is received in a helical channel formed in the instrument tip and that travels along (follows) the helical channel, so that axial movement of the actuator element in either direction causes rotation of the instrument tip in a clockwise or anticlockwise direction.

Figure 6:
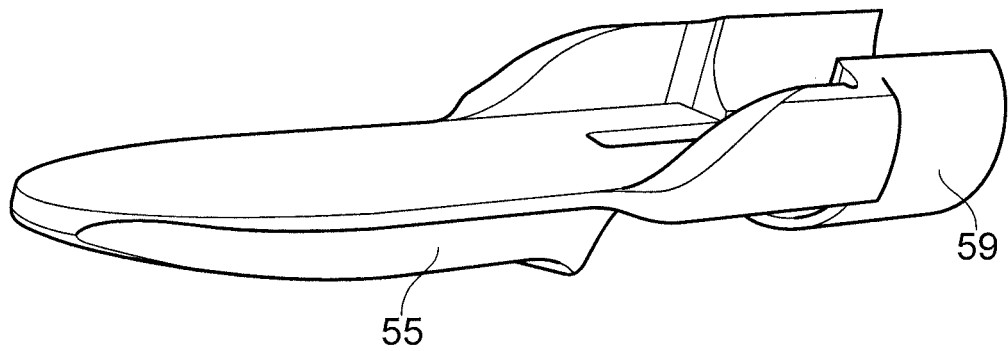
FIG. 6 is a schematic illustration of an instrument tip according to an embodiment of the present invention.
Figure 7:
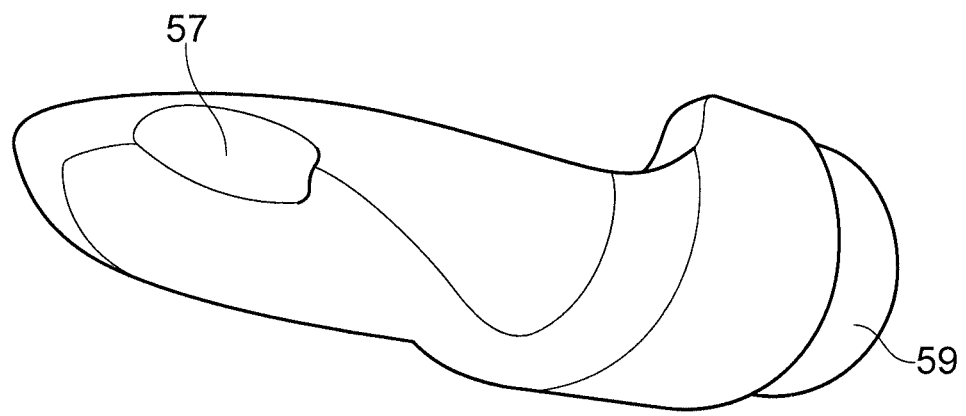
FIG. 7 is a schematic illustration of an instrument tip according to a further embodiment of the present invention.

FIGS. 6 and 7 show examples of instrument tips used in embodiments of the present invention in more detail. In FIG. 6, the cam surface (raised helical edge 55) is exposed and is therefore visible. In contrast, in FIG. 7 the cam surface (raised helical edge 55) is enclosed in a hull of the instrument tip and is therefore not visible. However, an exit hole 57 at a distal end of the raised helical edge 55 through which the actuator element can protrude from the end of the instrument tip is visible in FIG. 7. The exit hole 57 is adjacent a side surface of the instrument tip, so that the actuator element (e.g. a needle) will exit the instrument tip adjacent the side surface of the instrument tip. A seal may be provided in or around the cam surface and/or exit hole 57 to prevent the ingress of fluid into the tubular housing.

In both the embodiments of FIGS. 6 and 7 the instrument tips have axially extending shaft or shank portions 59 for being received in a distal end of a tubular housing, as discussed above.

Figure 8:
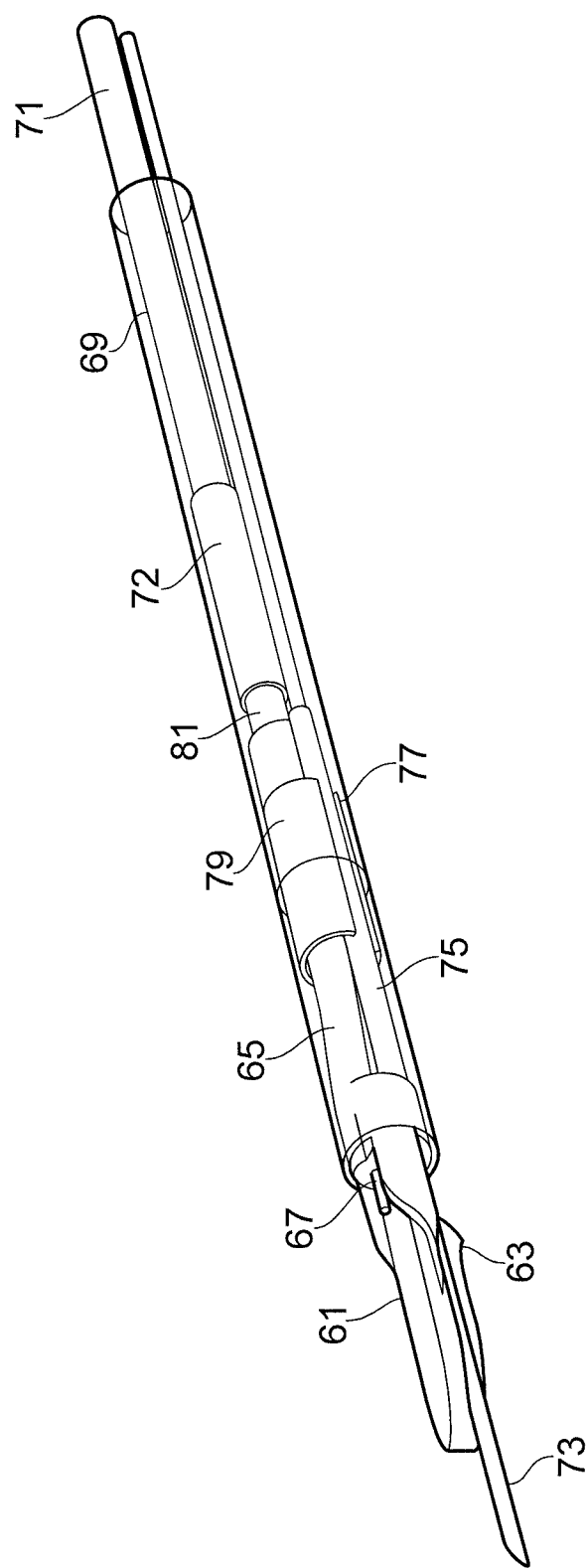
FIG. 8 is a schematic illustration of an electrosurgical instrument according to an embodiment of the present invention.

FIG. 8 is a schematic illustration of an electrosurgical instrument according to an embodiment of the present invention. Many of the features shown in FIG. 8 have been described in detail above, so only a concise description of those features is repeated here. It should be understood that the specific properties of the features shown in FIG. 8 may be the same as the specific properties of the corresponding features described above in relation to FIGS. 1 to 7.

In FIG. 8 the instrument tip 61 has the configuration shown in FIG. 6, with a cam surface (exposed raised helical edge 63) formed on a part of the external surface thereof.

The instrument tip 61 is fixed to a coaxial feed cable 65 for conveying radiofrequency energy and/or microwave frequency energy to the instrument tip. An inner conductor 67 of the coaxial feed cable 65 protrudes from a distal end of the coaxial feed cable 65 to contact a first conductive element on an upper surface of the instrument tip 61. Similarly, an outer conductor of the coaxial feed cable 65 is connected to a second conductive element on a bottom surface of the instrument tip 61.

The instrument tip 61 and the coaxial feed cable 65 are received within a tubular housing 69, shown as being transparent in FIG. 8 for ease of understanding.

The instrument tip 61 is rotatably mounted in the distal end of the tubular housing 69 so that the instrument tip and the coaxial feed cable 65 can rotate relative to the tubular housing 69. This is achieved by a shaft of shank portion of the instrument tip 61 being rotatably received in the distal end of the tubular housing 69.

The coaxial feed cable 65 is rotatably connected to a further coaxial feed cable 71 by a rotatable connection 72, such as that illustrated in FIGS. 1A to 1D, which allows rotation between the coaxial feed cable 65 and the further coaxial feed cable 71 while allowing the transmission of radiofrequency energy and/or microwave frequency energy there-between. Thus, the instrument tip 61 and coaxial feed cable 65 can be rotated within the tubular housing 69 relative to the further coaxial transmission line 71.

The cam surface/raised helical edge 63 is positioned to be contacted by a distal end of a needle 73 of the instrument when the needle 73 is moved axially along the instrument towards the instrument tip 61. Thus, axial movement of the needle 73 towards the instrument tip 61 so that a distal end of the needle contacts and applies force to the raised helical edge 63 causes rotation of the instrument tip 61 as described in detail above.

The needle 73 is configured for injecting fluid into tissue adjacent the instrument tip 61.

The needle 73 is slidably received in a needle guide tube 75 which passes along a slot 77 in a guide ring 79 that is fixed to the tubular housing 69. The slot 77 of the guide ring 79 constrains the movement of the needle 73 so that it can only move in the axial direction relative to the tubular housing 69, and not sideways.

The instrument further comprises a resilient sheath 81, for example made of silicone, which is fixed to the rotatable distal part and to the tubular housing 69, directly or indirectly. Thus, when the instrument tip 61 is rotated relative to the tubular housing 69, the resilient sheath is brought under tension and stores energy. The resilient sheath thus acts as a return spring that rotationally biases the distal part (and therefore the instrument tip 61) to return to an initial rotational orientation when it is rotated away from the initial rotational orientation, as described in detail above in relation to FIGS. 3A and 3B.

In FIG. 8 the needle 73 is shown in a position where it has been moved axially along the arrangement so that the distal end of the needle 71 is distal of the distal end of the instrument tip. In this configuration, the biasing force acting to rotate the instrument tip 61 is unable to cause rotation of the instrument tip 61, because the shaft of the needle 73 prevents rotation of the instrument tip 61.

Figure 9:
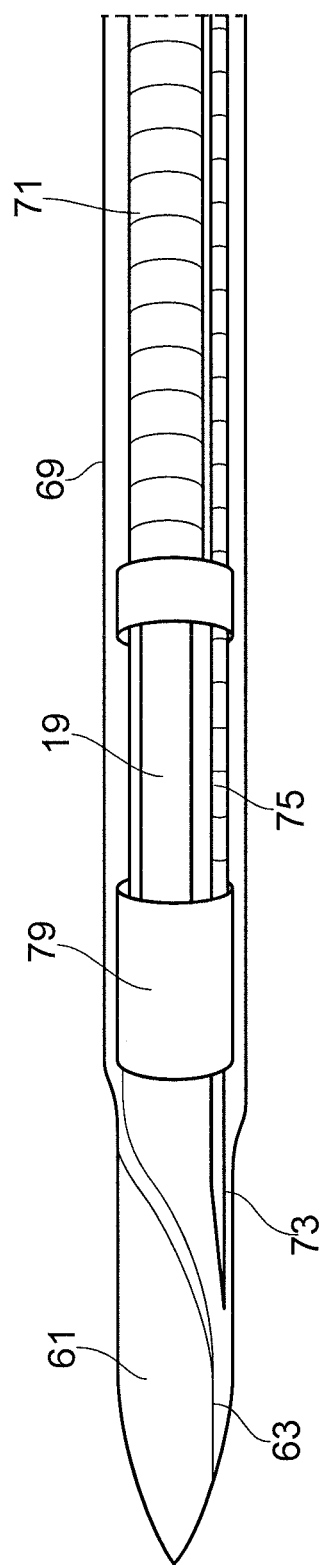
FIG. 9 is a sketch of an electrosurgical instrument according to an embodiment of the present invention.

FIG. 9 is a sketch of an electrosurgical instrument according to a further embodiment of the present invention. The mechanism for actuating rotation of the instrument tip used in this embodiment is the same as in FIGS. 3A to 8 so description thereof is not repeated and the same reference numbers are used. The primary difference in this embodiment is that the rotatable connection is the same as (or similar to) that shown in FIGS. 2A and 2B. In other words, a rotatable connection is formed between the instrument tip 61 and the coaxial feed cable 71 by a flexible transmission line 19 as described above. As in FIGS. 2A and 2B, the flexible transmission line 19 carries the radiofrequency energy and/or the microwave frequency energy from the coaxial feed cable 71 to the instrument tip 61.

The flexible transmission line 19 is resilient, so that when the needle is displaced axially along the instrument to contact the raised helical edge/cam surface 63 and rotate the instrument tip 61, the flexible transmission line 19 is twisted and stores mechanical energy because of this twisting. The twisted flexible transmission line 19 then provides a restoring force on the instrument tip 61 that acts to rotate the instrument tip 61 in the opposite direction back to its initial configuration.

The flexible transmission line 19 therefore allows rotation between the instrument tip 61 and the coaxial feed cable 71 and also acts as a return spring to return the instrument tip 61 to an initial rotational position when the instrument tip 61 is rotated relative to the coaxial feed cable 71 away from that initial position.

The flexible transmission strip 19 may therefore replace both the second coaxial feed cable and the spring in the embodiments illustrated in FIGS. 3A to 8. The other features of this embodiment and the corresponding advantages may be the same as the other features of the embodiments illustrated in FIGS. 3A to 8.

Of course, in other embodiments a torsion spring may also be provided around the flexible transmission line to provide the biasing force instead of, or in addition to, the biasing force provided by the flexible transmission line 19 in FIG. 9.

Figure 10:
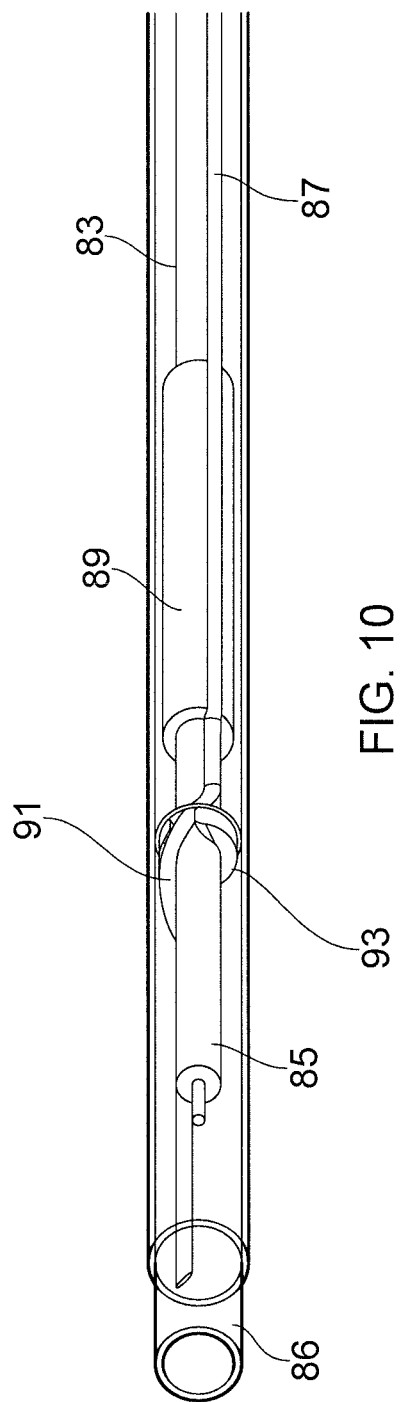
FIG. 10 is a schematic illustration of an electrosurgical instrument according to an embodiment of the present invention.

FIG. 10 shows an embodiment having an alternative mechanism for controlling rotation of the distal part of the instrument. The following description primarily relates to the rotation mechanism. This rotation mechanism may be combined with any of the rotatable connections described above in relation to the previously described embodiments, and this embodiment may have any of the features of the embodiments described above, where compatible.

The embodiment illustrated in FIG. 10 comprises a main coaxial feed cable 83, a proximal end of which will in practice be connected to a generator for supplying microwave frequency or radiofrequency energy. In FIG. 10, the distal end 85 of the main coaxial feed cable 83 is not connected to anything. In practice, the distal end 85 of the main coaxial feed cable 83 will be rotatably connected to a rotatable distal part of the instrument by a rotatable connection as described above in relation to any one of the previously described embodiments. For example, the distal end 85 of the main coaxial feed cable 83 may be rotatably connected to a distal coaxial cable by a rotatable connection as illustrated in FIGS. 1A to 1D. The distal coaxial cable may then be fixed to an instrument tip, so that the instrument tip and distal coaxial cable are together rotatable relative to the main coaxial feed cable 83 via the rotatable connection as a rotatable distal part of the instrument (e.g. as described above).

The embodiment illustrated in FIG. 10 has a tubular sleeve portion 86 that surrounds the distal end 85 of the main coaxial feed cable 83. In practice, the tubular sleeve portion 86 will be fixed to the rotatable distal part of the instrument, for example directly fixed to the instrument tip, so that the tubular sleeve portion 85 rotates together with the rotatable distal part of the instrument. The tubular sleeve portion may alternatively be referred to as a skirt portion or hollow cylindrical portion. In practice, it is not essential for the sleeve portion to have a tubular or cylindrical shape.

In the embodiment illustrated in FIG. 10, rotation of the distal part of the instrument, and therefore rotation of the instrument tip, is achieved by causing rotation of the sleeve portion 86 by axially displacing an actuator element 87 that is coupled to the sleeve portion 86 as described below. The actuator element 87 is rod-like or cable-like, and for example may be a needle for injecting liquid into tissue adjacent to the instrument tip.

The actuator element 87 is prevented from moving in any direction other than an axial direction relative to the main coaxial feed cable 83 by an actuator guide 89 (needle guide).

The actuator guide 89 comprises a tubular or ring-like member fixed to the main coaxial feed cable 83 (and/or to an external housing) that has an axial channel or slot in which the actuator is slidably received. Thus, the actuator element 87 is able to move only in the axial direction relative to the main coaxial feed cable 83.

The actuator element 87 has a helical portion 91, wherein the actuator is formed in, or bent into, a helical shape. The helical portion 91 is arranged around the outer surface of the main coaxial feed cable 83.

The tubular sleeve portion 86 has a follower 93 adjacent its proximal end that follows a helical path defined by the helical portion 91 as the actuator element 87 is moved axially relative to the main coaxial feed cable 83. As shown more clearly in the enlarged view of FIG. 11, the follower 93 comprises a ring fixed to an inner surface of the tubular sleeve portion 86 that surrounds the main coaxial feed cable 83 and that has a channel or slot 95 through which the helical portion 91 of the actuator element 87 passes.

The tubular sleeve portion is prevented from moving axially relative to the main coaxial feed cable 83, for example by one or more axial stops. Therefore, as the actuator element 87 is moved axially, the axial movement of the helical portion of the actuator through the channel or slot 95 of the follower 93, which is prevented from moving axially, causes rotation of the follower 93, the direction of the rotation depending on the axial direction of movement of the actuator element 87. Rotation of the follower 93 causes rotation of the tubular sleeve portion 86, because they are fixed together. Furthermore, rotation of the tubular sleeve portion 86 causes rotation of the distal end of the instrument, because the tubular sleeve portion 86 is fixed to the distal end of the instrument, for example by being directly fixed to the instrument tip. Thus, axial movement of the actuator element 87 causes rotation of the instrument tip, the direction of rotation of the instrument tip depending on the axial direction of movement of the actuator element 87.

An important difference between this embodiment and the previously described embodiments is that the interaction between the helical portion 91 and the follower 93 is such that movement of the actuator element 87 in either axial direction causes rotation of the instrument tip. For example, movement of the actuator element 87 in the distal axial direction may cause clockwise rotation of the instrument tip, whereas movement of the actuator element 87 in the proximal axial direction may cause anticlockwise (counter clockwise) rotation of the instrument tip, or the other way around.

Thus, with this embodiment it is not necessary to provide a biasing means to return the instrument tip to a predetermined rotational position once it has been rotated by axial movement of the actuator element 87, because the instrument tip can instead be returned to an initial rotational position by moving the actuator element 87 axially back to an initial axial position. In other words, the actuator element 87 can be used to rotate the instrument tip in either direction.

Suitable electrical connections can be maintained between the main coaxial feed cable 83 and the instrument tip during the rotation by providing a rotatable connection between the distal end 85 of the main coaxial feed cable 83 and the instrument tip, e.g. with a rotatable connection as described above in relation to any one of the previously described embodiments.

Figure 11:
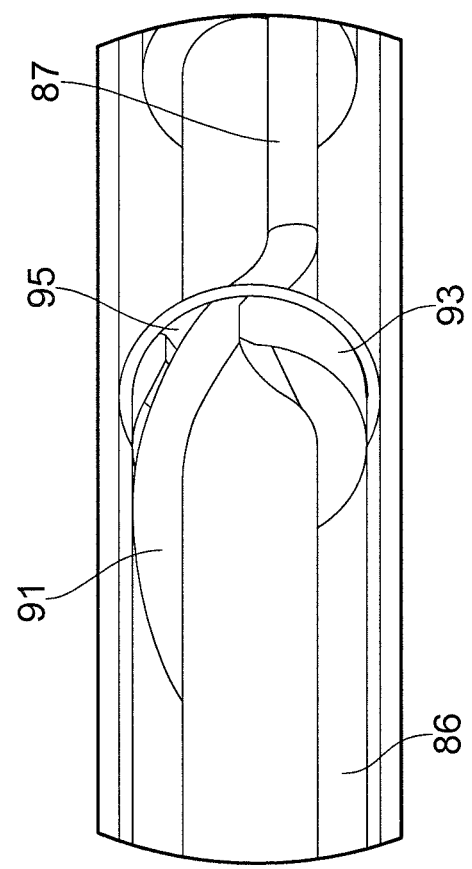
FIG. 11 is an enlarged schematic illustration of the portion of the electrosurgical instrument of FIG. 10 shown with the circle in FIG. 10.

As shown in FIGS. 10 and 11, an outer sheath may be present to enclose the main coaxial feed cable 83, actuator 87 and the other components illustrated in FIGS. 10 and 11.

An electrosurgical instrument according to a further embodiment of the present invention is illustrated in FIG.

12. The embodiment of FIG. 12 has a different mechanism for achieving rotation of an instrument tip of an electrosurgical instrument to the previously described embodiments.

Figure 12:
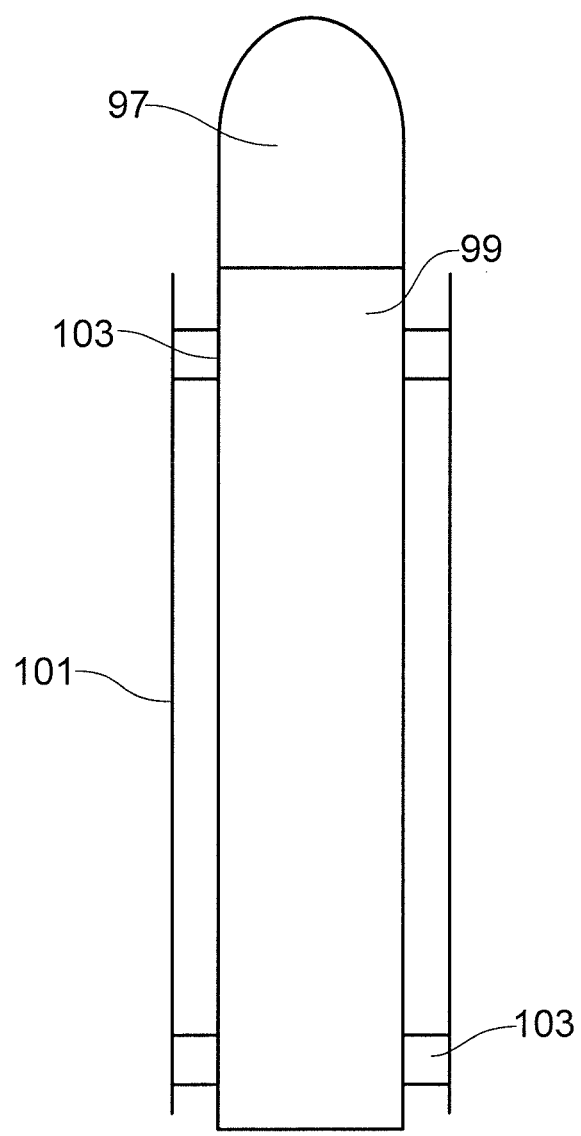
FIG. 12 is a schematic illustration of an electrosurgical instrument according to a further embodiment of the present invention.

In the embodiment of FIG. 12, an electrosurgical instrument tip 97 is fixed at the distal end of a coaxial feed cable 99, so that the instrument tip 97 cannot rotate relative to the coaxial feed cable 99. The inner and outer conductors of the coaxial feed cable 99 are connected to respective conductive elements of the instrument tip 97, for example as described above in relation to the previously described embodiments.

The coaxial feed cable 99 is located within a tubular housing or sheath 101. Bearings 103 are positioned between the coaxial feed cable 99 and the sheath 101, so that the coaxial feed cable 99 is rotatable within the sheath 101. In the embodiment shown in FIG. 12 two bearings 103 are provided, one adjacent the proximal end of the sheath 101 and one adjacent the distal end of the sheath 101. However, in other embodiments the bearings 103 may be located differently, and/or further bearings 103 may be provided. For example, providing additional bearings 103 to the bearings 103 shown in FIG. 12 may ensure smooth rotation of the coaxial feed cable 99 within the sheath 101, for example when the sheath 101 and therefore the coaxial feed cable 99 are bent. Without the provision of further bearings 103, it is possible that in some circumstances the coaxial feed cable 99 may come into contact with the sheath 101 when the sheath 101 is bent, restricting rotation of the coaxial cable 99 within the sheath 101.

The presence of the bearings 103 mean that the instrument tip 97 can be rotated relative to the sheath 101 by rotating the entire coaxial feed cable 99 within the sheath 101 relative to the sheath 101. Any suitable type of bearing may be used as the bearing 103, for example rolling element bearings that include rolling elements such as ball bearings, or brush bearings.

A seal may be provided adjacent the distal end of the sheath 101 to prevent the ingress of fluid into the sheath 101.

The bearings 103 may have axially aligned partial circumferential cuts, channels or openings to allow a needle for injecting fluid into tissue adjacent to the instrument tip 97 to be fed along the sheath 101.

In any of the embodiments described above, the instrument tip may be a half-wave resonator/half-wave section. In other words, the instrument tip may have a length that is substantially equal to $$\frac{\lambda}{2},$$

where $\lambda$ is the wavelength of microwave frequency energy having a predetermined frequency in the instrument tip. The predetermined frequency may be 5.8 GHz. Thus, the instrument tip may essentially be transparent to the impedance of the tissue load.

With such an instrument tip, an impedance matching section may also be provided to match an impedance of the tissue load at the instrument tip to the impedance of the coaxial feed cable at the predetermined frequency. The impedance matching section may comprise an impedance transformer. The length of the impedance transformer may be substantially equal to $$(2n+1)\frac{\lambda}{4},$$

where n is an integer number greater than or equal to zero and $\lambda$ is the wavelength of the microwave frequency energy in the impedance transformer at the predetermined frequency. The impedance transformer may match a real part of the impedance of the tissue load to a real part of the impedance of the coaxial feed cable.

The impedance matching section may further comprise a section of coaxial transmission line between the impedance transformer and a proximal end of the instrument tip. The section of coaxial transmission line may have a length configured to effectively remove a reactive (imaginary) part of the impedance of the tissue load. In this case, the impedance transformer may match a real part of the impedance of the tissue load as modified by the section of coaxial transmission line to the real part of the impedance of the coaxial feed cable.

The impedance of the section of coaxial transmission line may be the same as the impedance of the coaxial feed cable, for example 50 Ohms.

In an alternative arrangement for matching an impedance of the tissue load at the instrument tip to the impedance of the coaxial feed cable at the predetermined frequency, a characteristic impedance of the instrument tip may be substantially equal to a characteristic impedance of the coaxial feed cable. Furthermore, the distal part may comprise an impedance matching section for matching the characteristic impedance of the coaxial feed cable to the impedance of a tissue load in contact with the instrument tip at the predetermined frequency of microwave frequency energy. The impedance matching section may comprise a length of coaxial transmission line connected to a proximal end of the instrument tip, and a short circuited stub. Again, the short length of coaxial transmission line may essentially remove a reactive (imaginary) component of the impedance of the tissue load, and the short circuited stub may then match the remaining real impedance to the impedance of the coaxial feed line.

In an alternative arrangement for matching an impedance of the tissue load at the instrument tip to the impedance of the coaxial feed cable at the predetermined frequency, the impedance matching may be achieved by a two or three stub tuner.

The invention claimed is:

1. An electrosurgical instrument for applying radiofrequency energy and/or microwave frequency energy to biological tissue, the instrument comprising:
    an instrument tip for applying radiofrequency energy and/or microwave frequency energy to biological tissue;
    a coaxial feed cable for conveying radiofrequency energy and/or microwave frequency energy to the instrument tip;
    a sheath surrounding the coaxial feed cable; and
    a plurality of rolling element bearings or brush bearings positioned between the coaxial feed cable and the sheath for enabling rotation of the coaxial feed cable relative to the sheath.

2. The electrosurgical instrument according to claim 1, wherein a length of the instrument tip is substantially equal to $\lambda/2$, where $\lambda$ is wavelength of microwave frequency energy having a predetermined frequency in the instrument tip.

3. The electrosurgical instrument according to claim 1, wherein:
    a characteristic impedance of the instrument tip is substantially equal to a characteristic impedance of the coaxial feed cable; and a distal part comprises an impedance matching section for matching the characteristic impedance of the coaxial feed cable to the impedance of a tissue load in contact with the instrument tip at a predetermined frequency of microwave frequency energy, wherein the impedance matching section comprises:
   a length of coaxial transmission line connected to a proximal end of the instrument tip; and
   a short circuited stub.

4. The electrosurgical instrument according to claim 1, wherein a distal part comprises an impedance transformer that substantially matches a characteristic impedance of a coaxial transmission line to a characteristic impedance of a tissue load in contact with the instrument tip at a predetermined frequency.

5. The electrosurgical instrument according to claim 1, wherein the bearings comprise axially aligned partial circumferential cuts, channels or openings for feeding a needle for injecting fluid into tissue adjacent to the instrument tip along the sheath.

6. The electrosurgical instrument according to claim 1, wherein a seal is provided adjacent a distal end of the sheath for preventing an ingress of fluid into the sheath.

* * * * *